(12) United States Patent
Lee et al.

(10) Patent No.: US 11,622,838 B2
(45) Date of Patent: Apr. 11, 2023

(54) METHOD OF MANUFACTURING DENTAL IMPLANT PLACEMENT GUIDE, AND PRELIMINARY GUIDE AND GUIDE TRAY THEREFOR

(71) Applicant: IMSOL CORP., Gyeonggi-do (KR)

(72) Inventors: Yun Ho Lee, Gyeonggi-do (KR); Da Som Heo, Gyeonggi-do (KR); Heui Jung Yang, Gyeonggi-do (KR)

(73) Assignee: IMSOL CORP, Gyeonggi-Do (KR)

( * ) Notice: Subject to any disclaimer, the term of this patent is extended or adjusted under 35 U.S.C. 154(b) by 483 days.

(21) Appl. No.: 16/548,205

(22) Filed: Aug. 22, 2019

(65) Prior Publication Data
US 2020/0205938 A1    Jul. 2, 2020

(30) Foreign Application Priority Data

Dec. 26, 2018 (KR) .......... 10-2018-0169173
May 13, 2019 (KR) .......... 10-2019-0055759

(51) Int. Cl.
*A61C 9/00* (2006.01)
*A61C 8/00* (2006.01)
*A61B 6/14* (2006.01)
*A61B 6/03* (2006.01)

(52) U.S. Cl.
CPC .......... *A61C 8/0001* (2013.01); *A61B 6/032* (2013.01); *A61B 6/145* (2013.01); *A61C 8/009* (2013.01); *A61C 9/0006* (2013.01)

(58) Field of Classification Search
CPC .................................. A61C 9/0006
See application file for complete search history.

(56) References Cited

U.S. PATENT DOCUMENTS

| | | | | |
|---|---|---|---|---|
| 3,473,225 A | * | 10/1969 | Walker | A61C 9/0006 433/48 |
| 5,890,894 A | * | 4/1999 | Mio | A61C 9/0006 433/37 |
| 6,071,121 A | * | 6/2000 | Simon | A61C 7/08 433/37 |
| 6,302,690 B1 | * | 10/2001 | Brandhorst | A61C 9/0006 433/41 |
| 8,308,480 B2 | * | 11/2012 | Bublewitz | A61C 9/0006 433/48 |
| 8,465,281 B2 | * | 6/2013 | Haselhuhn | A61C 8/0001 433/37 |
| 9,827,075 B2 | * | 11/2017 | Chun | A61C 19/05 |

FOREIGN PATENT DOCUMENTS

| | | |
|---|---|---|
| CN | 107928821 | 4/2018 |
| KR | 1020100042912 | 4/2010 |
| KR | 10-0990742 | 10/2010 |
| KR | 10-2010-0117385 | 11/2010 |

(Continued)

OTHER PUBLICATIONS

First Office Action for CN App. No. 201980086608.1, dated Feb. 9, 2022, 31 pages w/ English Translation.

*Primary Examiner* — Ralph A Lewis
(74) *Attorney, Agent, or Firm* — Adsero IP

(57) ABSTRACT

Disclosed herein is a preliminary guide including an impression resin and a guide tray. The guide tray includes an impression resin accommodation part, a jig fastening part, a protective cover part, and a grip part.

11 Claims, 26 Drawing Sheets

(56) References Cited

FOREIGN PATENT DOCUMENTS

| KR | 101092907 | 12/2011 | | |
|----|----|----|----|----|
| KR | 10-1481305 | 1/2015 | | |
| KR | 10-2016-0136133 | 11/2016 | | |
| KR | 10-2019-0055759 | 5/2019 | | |
| WO | WO-2007142474 A2 * | 12/2007 | ........... | A61C 9/0006 |

* cited by examiner

METHOD OF MANUFACTURING DENTAL IMPLANT PLACEMENT GUIDE, AND PRELIMINARY GUIDE AND GUIDE TRAY THEREFOR

CROSS-REFERENCE TO RELATED APPLICATIONS

This application claims priority to and the benefit of Korean Patent Application Nos. 10-2018-0169173, filed on Dec. 26, 2018, and 10-2019-0055759, filed on May 13, 2019, the disclosures of which are incorporated herein by reference in their entirety.

BACKGROUND OF THE INVENTION

Field of the Invention

The present invention relates to a method of manufacturing a dental implant placement guide used to more safely and accurately perform dental implant surgery, and a preliminary guide and a guide tray therefor.

Description of the Related Art

Dental implant surgery involves placing a dental implant fixture in an alveolar bone. In the field of surgery, a placement or surgical guide is used that is manufactured in various ways to securely and accurately place the dental implant fixture.

A representative example of the placement guide is disclosed in Korean Patent No. 10-1797155 entitled "Method of Manufacturing Surgical Guide and Abutment for Dental Implant", and its configuration is illustrated in FIG. 1.

FIG. 1 is a flowchart illustrating a conventional method of manufacturing a surgical guide for a dental implant.

As illustrated in FIG. 1, the conventional method includes: a first step s10 of obtaining a primary scanning image and an oral CT image by scanning the inside of the subject's oral cavity and of obtaining a secondary scanning image by scanning the outer surface of the occlusal resin produced in consideration of the occlusion height between a region of a tooth to be placed and an opposing tooth;

a second step s20 of obtaining an integrated scanning image with the occlusion height of the subject considered by preliminarily matching the primary scanning image and the secondary scanning image based on the common portion displayed thereon;

a third step s30 of obtaining a three-dimensional occlusal guide image by overlapping and finally matching the integrated scanning image and the oral CT image based on the matching marker image included therein; and a fourth step s40 of setting the height of a crown based on the three-dimensional occlusal guide image and producing a surgical guide.

The conventional method of manufacturing a surgical guide is problematic in that operation itself is complicated and operating time is long because it requires multiple scanning operations, an operation of integrating the scanned images, and an operation of matching the integrated scanning image and the CT image.

In addition, there is a problem in that the accuracy or precision of the guide as an end product is not constant due to irregularity and/or accumulation of errors that may occur at each operation.

CITATION LIST

Patent Literature

Patent Literature 1: Korean Patent No. 10-1797155

SUMMARY OF THE INVENTION

The present invention has been made in view of the above-mentioned problem, and it is an object of the present invention to provide a method of manufacturing a dental implant placement guide, in which operation can be significantly simplified, operating time can be significantly reduced, and accuracy or precision of a guide as an end product can be kept constant by utilizing only a CT image without an oral scan image, and a preliminary guide and a guide tray therefor.

In accordance with one aspect of the present invention, there is provided a method of manufacturing a dental implant placement guide, which includes applying a preliminary guide to a patient's implant placement region and obtaining a CT image, designing implant placement information to be suitable for the placement region using the CT image, and completing a guide by forming a guide hole in the preliminary guide according to the designed placement information.

In accordance with another aspect of the present invention, there is provided a method of manufacturing a dental implant placement guide, which includes applying a preliminary guide to a patient's implant placement region, partially curing an impression resin with the preliminary guide held, removing the preliminary guide from the placement region and fully curing the partially cured impression resin, reapplying the preliminary guide to the patient's implant placement region and obtaining a CT image, designing implant placement information to be suitable for the placement region using the CT image, and completing a guide by forming a guide hole in the preliminary guide according to the designed placement information.

In accordance with still another aspect of the present invention, there is provided a preliminary guide that includes an impression resin used to mold an implant placement region in a pattern form, and a guide tray including an impression resin accommodation part configured to accommodate the impression resin therein, and a jig fastening part fastened to a working jig in processing equipment when a placement guide hole is machined to complete a guide.

In accordance with a further aspect of the present invention, there is provided a guide tray that includes an impression resin accommodation part configured to accommodate an impression resin therein, and a jig fastening part fastened to a working jig in processing equipment when a placement guide hole is machined to complete a guide.

The impression resin accommodation part may have a shape corresponding to an upper incisor/premolar region or a lower incisor/premolar region, a shape corresponding to an upper central incisor to second molar region or a lower central incisor to second molar region, a shape corresponding to an upper premolar/molar region or a lower premolar/molar region, or a shape corresponding to an upper central incisor to second molar region or a lower central incisor to second molar region.

DETAILED DESCRIPTION OF THE PREFERRED EMBODIMENTS

Hereinafter, methods of manufacturing a dental implant placement guide according to the present invention and a preliminary guide and a guide tray for manufacturing a guide according to various embodiments will be described in detail with reference to the accompanying drawings.

First, basic and modified methods of manufacturing a dental implant placement guide according to the present invention will be described with reference to FIGS. 2 and 3. The basic and modified manufacturing methods are selectively and advantageously applicable according to the properties of an impression resin, in particular, the curing properties thereof.

Figure 1:
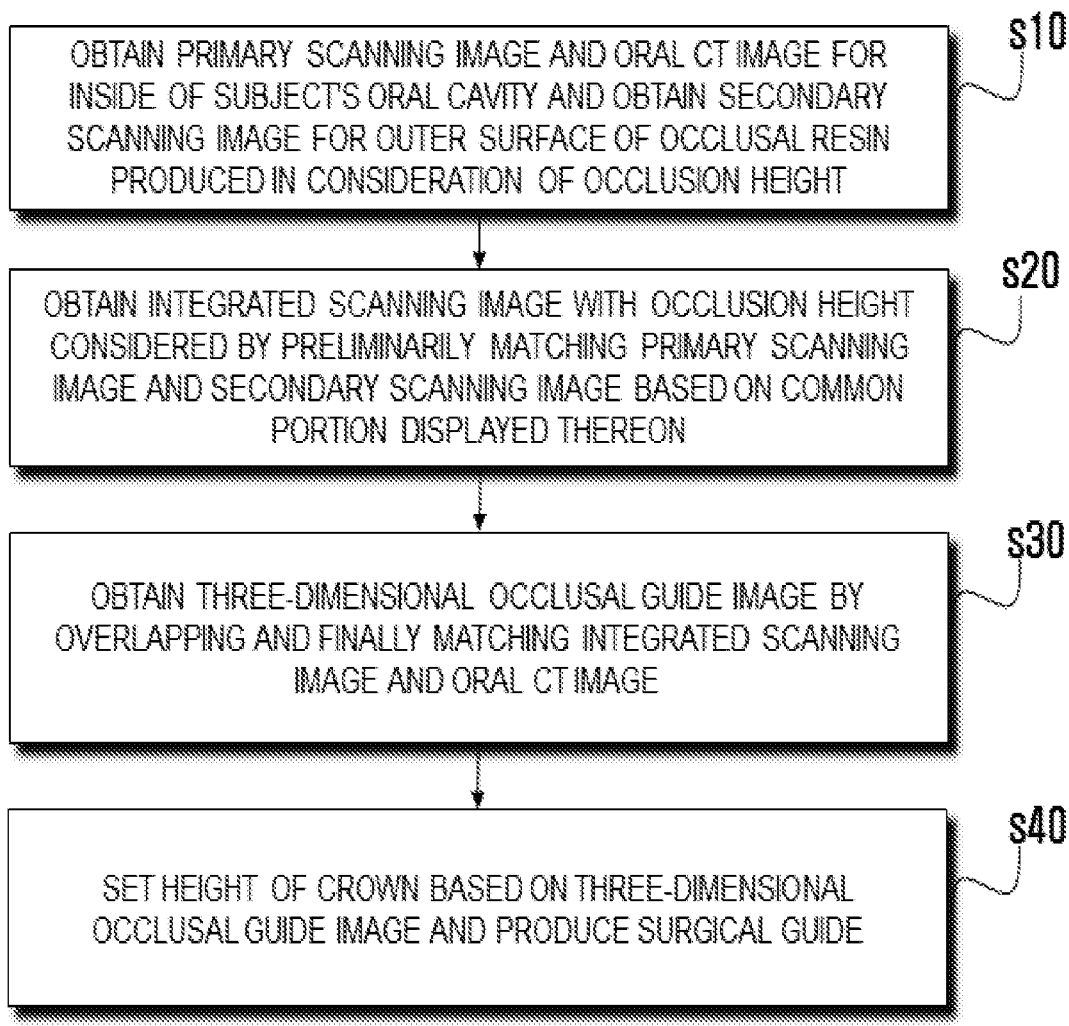
FIG. 1 is a flowchart illustrating a conventional method of manufacturing a surgical guide and an abutment for a dental implant.
Figure 2:
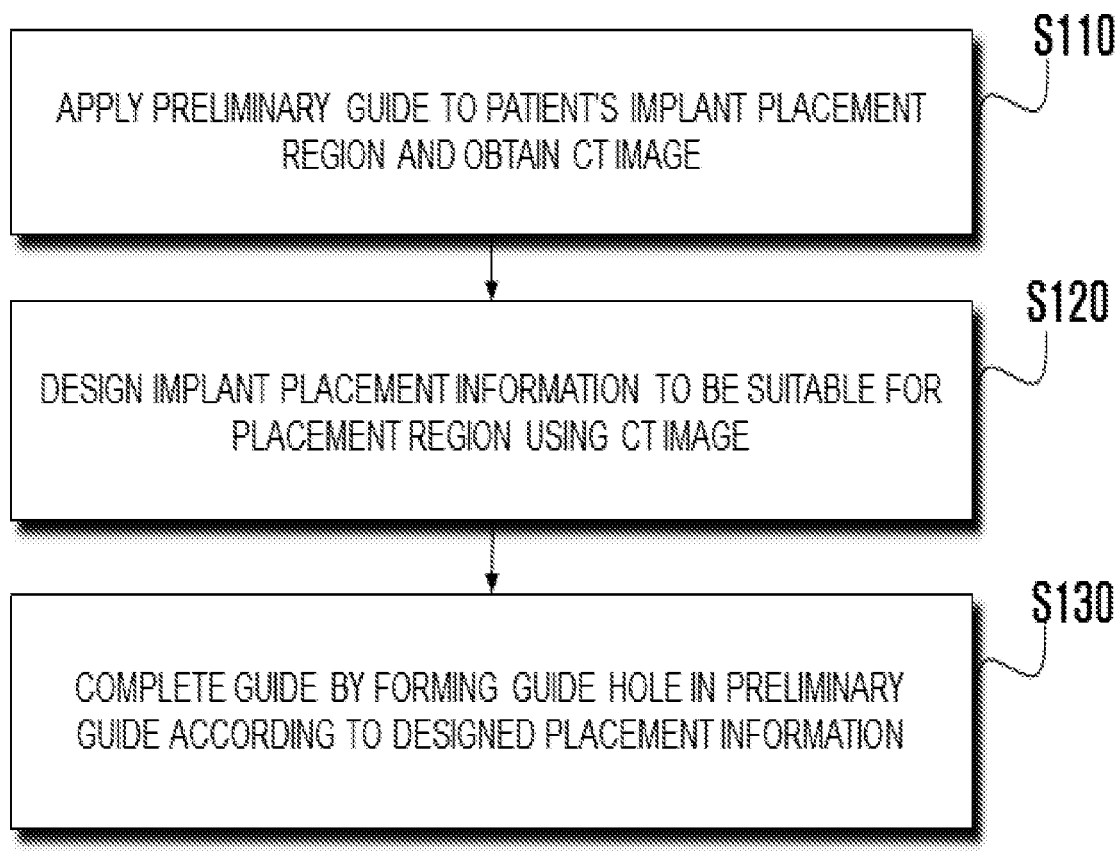
FIG. 2 is a flowchart illustrating a basic method of manufacturing a dental implant placement guide according to the present invention.
Figure 3:
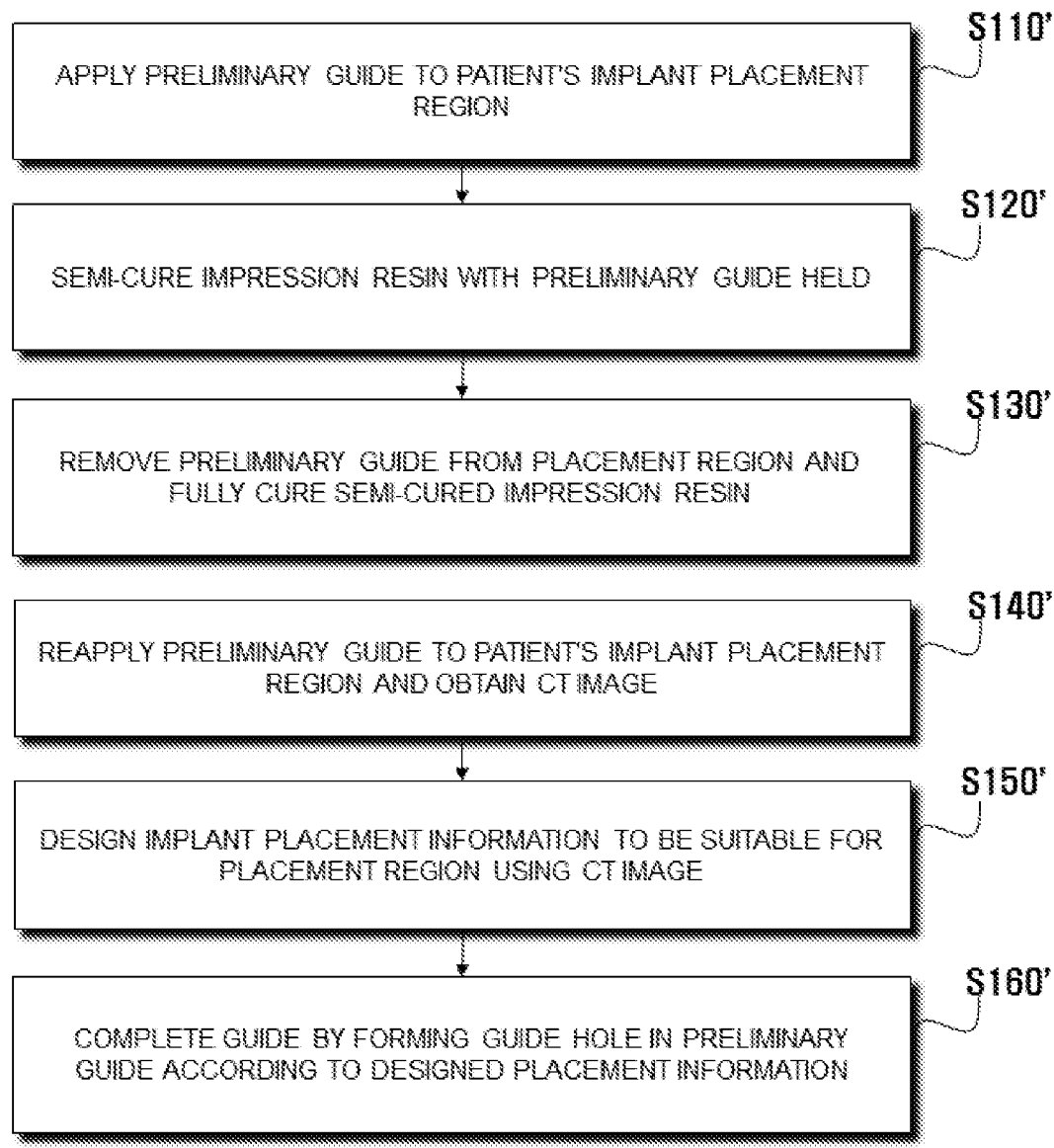
FIG. 3 is a flowchart illustrating a modified method of manufacturing a dental implant placement guide according to the present invention.

FIGS. 2 and 3 are flowcharts illustrating basic and modified methods of manufacturing a dental implant placement guide according to the present invention.

Basic Manufacturing Method (3 Steps)

As illustrated in FIG. 2, the basic manufacturing method of the present invention includes three steps.

In a first step S110, a preliminary guide is applied to a patient's implant placement region and a CT image is obtained.

In this case, the placement region is molded in a pattern form in an impression resin in the preliminary guide. The molded pattern is used as a means for physically matching the placement region with a guide to be finally completed. This physical matching allows for very high accuracy and precision and significantly shortened operating time, compared to the conventional digital matching between the integrated image of the scan image and the CT image and the placement region.

In a second step S120, implant placement information is designed to be suitable for the placement region using the CT image.

In this case, a design program is used to design the placement information, such as the type and size of the implant, the placement position, placement depth, and placement angle of the implant, etc. in consideration of an occlusal relationship by loading the CT image on the design program.

In a third step S130, the guide is completed by forming a guide hole in the preliminary guide according to the designed placement information.

In this case, a preliminary guide image coinciding with the preliminary guide held by the patient in the first step S110 is selected on the design program and placed on the CT image having the designed placement information. The guide hole is then designed in the preliminary guide image according to the placement information to generate digital information for processing. Finally, the guide is completed by machining the guide hole in the preliminary guide according to the digital information in processing equipment.

Modified Manufacturing Method (6 Steps)

As illustrated in FIG. 3, the modified manufacturing method of the present invention includes six steps.

In a first step S110', a preliminary guide is applied to a patient's implant placement region.

In this case, a practitioner selects a preliminary guide suitable for the placement region from among various preliminary guides. After the practitioner places the preliminary guide on the placement region and softly presses it with his/her finger to place the preliminary guide in position to some extent, the patient closes his/her mouth with proper force to hold the preliminary guide.

In a second step S120', an impression resin is partially cured with the preliminary guide held.

For the partial curing, the preliminary guide is irradiated with light. Preferably, halogen or LED light having a wavelength of 400 nm to 500 nm and an intensity of 800 mW/cm$^2$ to 1,000 mW/cm$^2$ is used as the light. Preferably, the light is radiated slowly from the side surface to the top surface of the preliminary guide for 30 seconds to 60 seconds.

The partial curing is to ensure that the pattern molded in the soft impression resin is kept well when the preliminary guide is removed from the placement region and that there is no problem in removing the preliminary guide by the undercut of the placement region. If there is an undercut when full curing is performed, the preliminary guide may not be normally removed due to the undercut.

Although the impression resin is partially cured with the preliminary guide held in the present embodiment, it is preferable that the impression resin is cured as much as possible as long as the tooth is damaged due to curing heat or the preliminary guide is able to be normally removed by the undercut. When the impression resin is sufficiently cured with the preliminary guide held, the molded pattern is kept better, which will enhance the completion of physical matching performed later on.

In a third step S130', the preliminary guide is removed from the placement region and the partially cured impression resin is fully cured.

For the full curing, the light used in the second step is radiated slowly to the top, side, and bottom surfaces of the preliminary guide for 40 seconds to 80 seconds. In the development process, we found that the overall shrinkage degree of the impression resin may be changed depending on the order of the surface to be irradiated because the impression resin is shrunk due to high heat generated when it is irradiated with light. Through many experiments, we found that the molded pattern can be most preferably used for physical matching since it is shrunk to the least degree when light is radiated in the order of the top, side, and bottom surfaces of the preliminary guide.

After the first, second, and third steps, the placement region is molded in a pattern form in the impression resin in the preliminary guide. The molded pattern is used as a means for physically matching the placement region with a guide to be finally completed. This physical matching allows for very high accuracy and precision and significantly shortened operating time, compared to the conventional digital matching between the integrated image of the scan image and the CT image and the placement region.

In a fourth step S140', the preliminary guide is reapplied to the patient's implant placement region and a CT image is obtained.

In this case, the preliminary guide is held on the placement region such that the pattern molded in the impression resin is physically matched with the placement region.

In a fifth step S150', implant placement information is designed to be suitable for the placement region using the CT image.

In this case, a design program is used to design the placement information, such as the type and size of the implant, the placement position, placement depth, and placement angle of the implant, etc. in consideration of an occlusal relationship by loading the CT image on the design program.

In a sixth step S160', the guide is completed by forming a guide hole in the preliminary guide according to the designed placement information.

In this case, a preliminary guide image coinciding with the preliminary guide held by the patient in the first step S110' is selected on the design program and placed on the CT image having the designed placement information. The guide hole is then designed in the preliminary guide image according to the placement information to generate digital information for processing. Finally, the guide is completed by machining the guide hole in the preliminary guide according to the digital information in processing equipment.

Next, various embodiments of a preliminary guide and a guide tray used for the method of manufacturing a dental implant placement guide according to the present invention described above will be described with reference to the other accompanying drawings. For reference, a tooth structure is illustrated in FIG. 4 for better understanding the description of the present invention.

First Embodiment

Figure 5A:
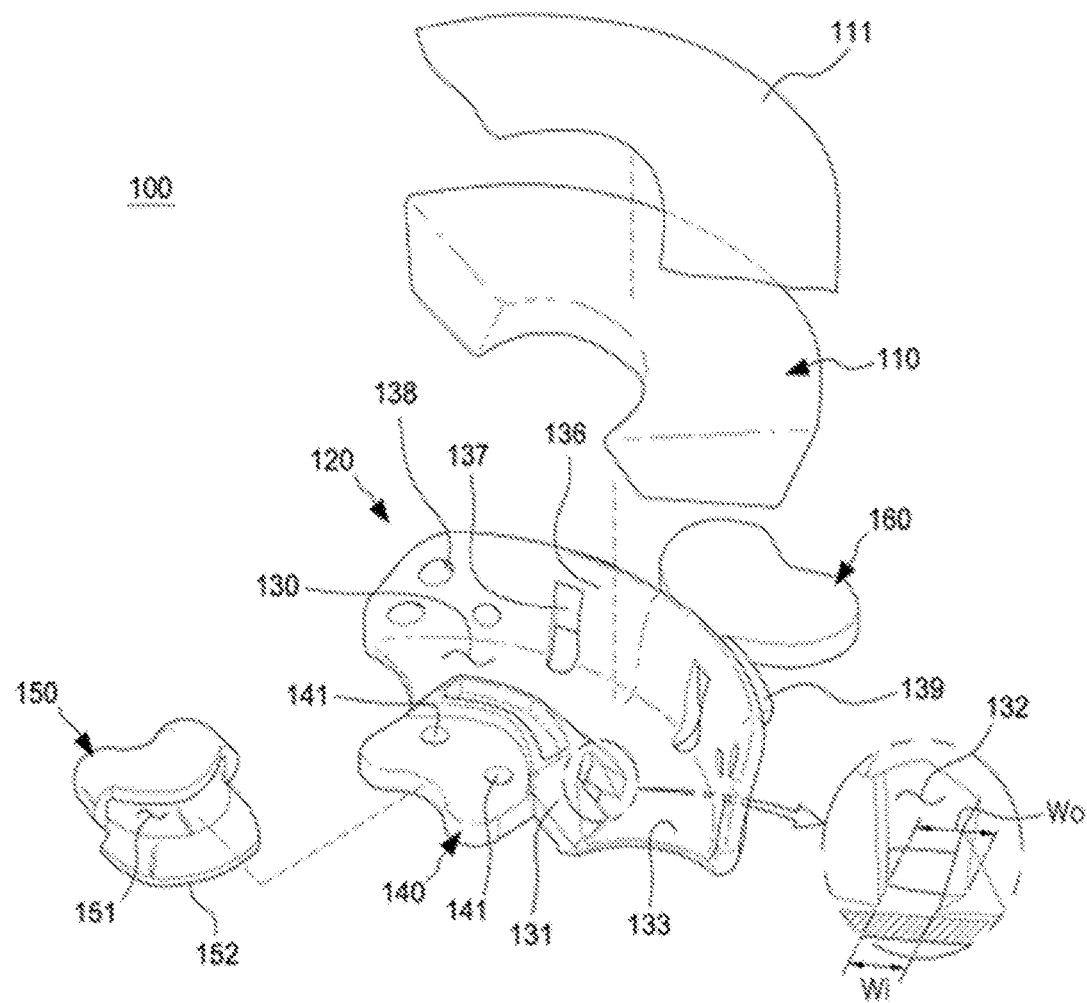
FIGS. 5A and 5B are exploded perspective views of a first preferred embodiment of a preliminary guide and a guide tray for manufacturing the guide of FIG. 2 or 3 when viewed from different sides.
Figure 5B:
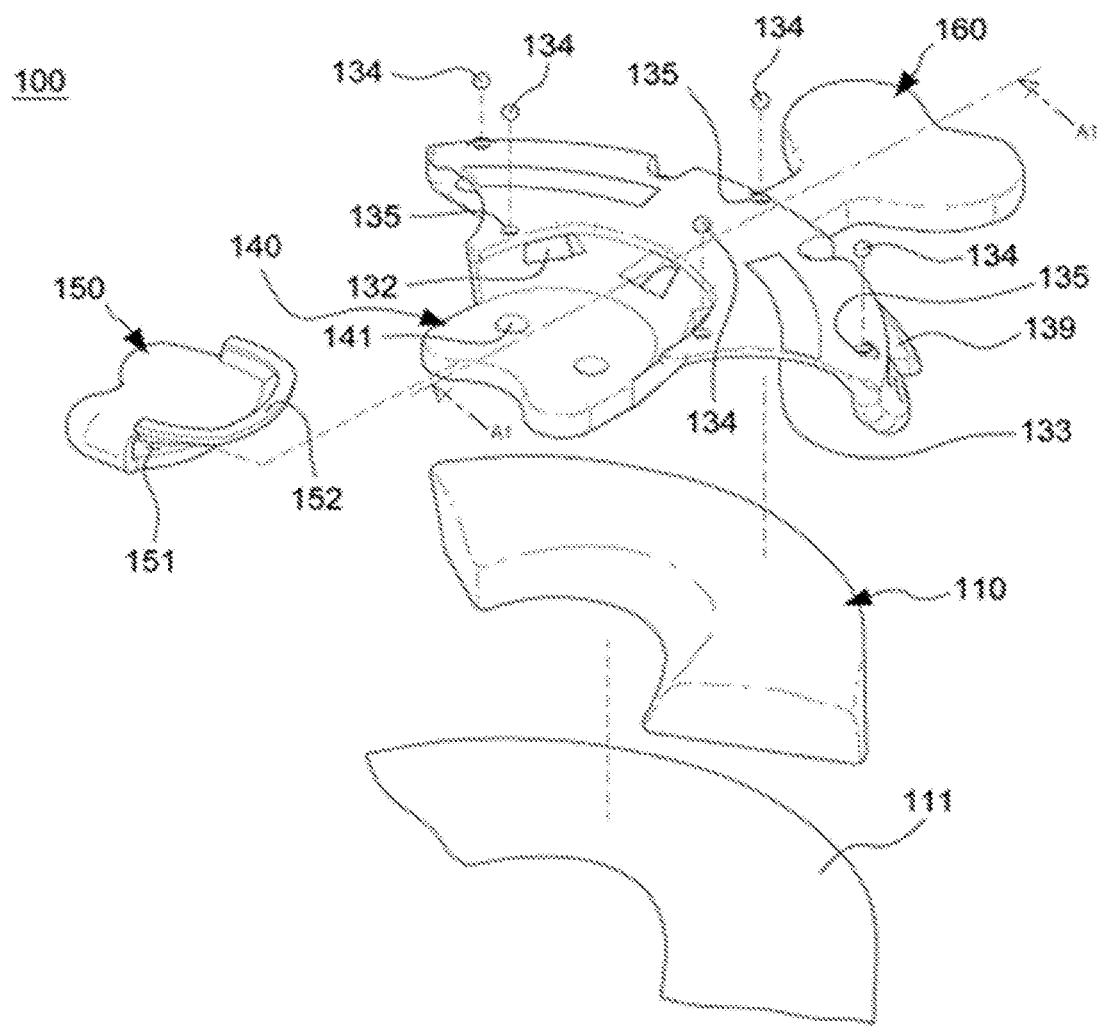
Figure 5C:
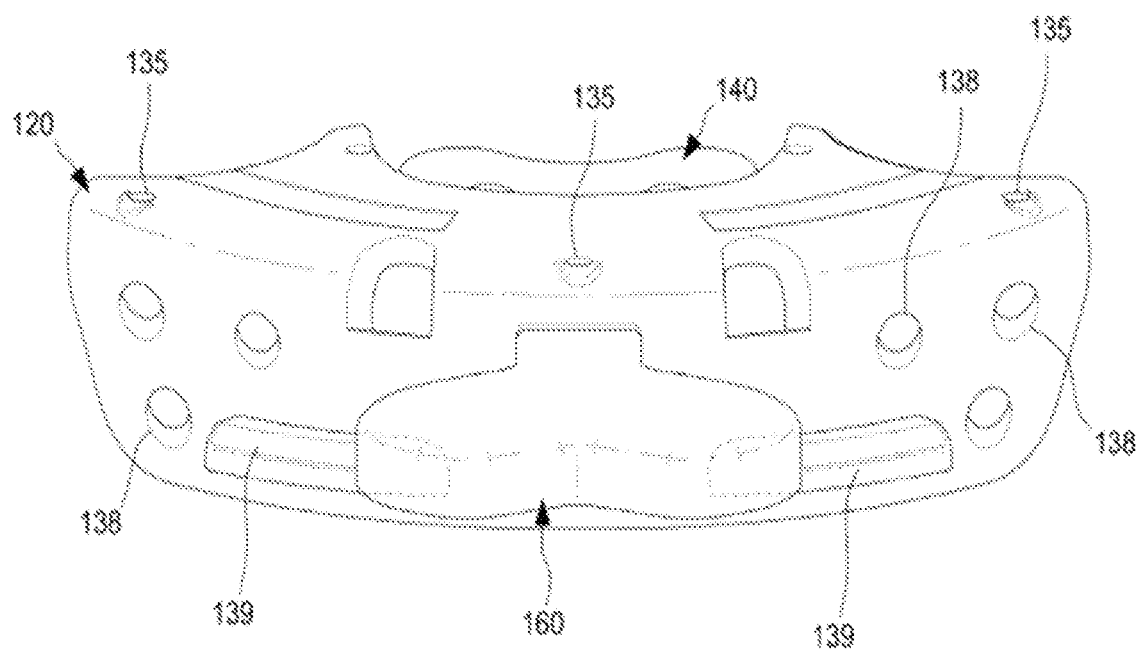
FIG. 5C is a view looking at a grip part of the guide tray of FIG. 5A or 5B.
Figure 5D:
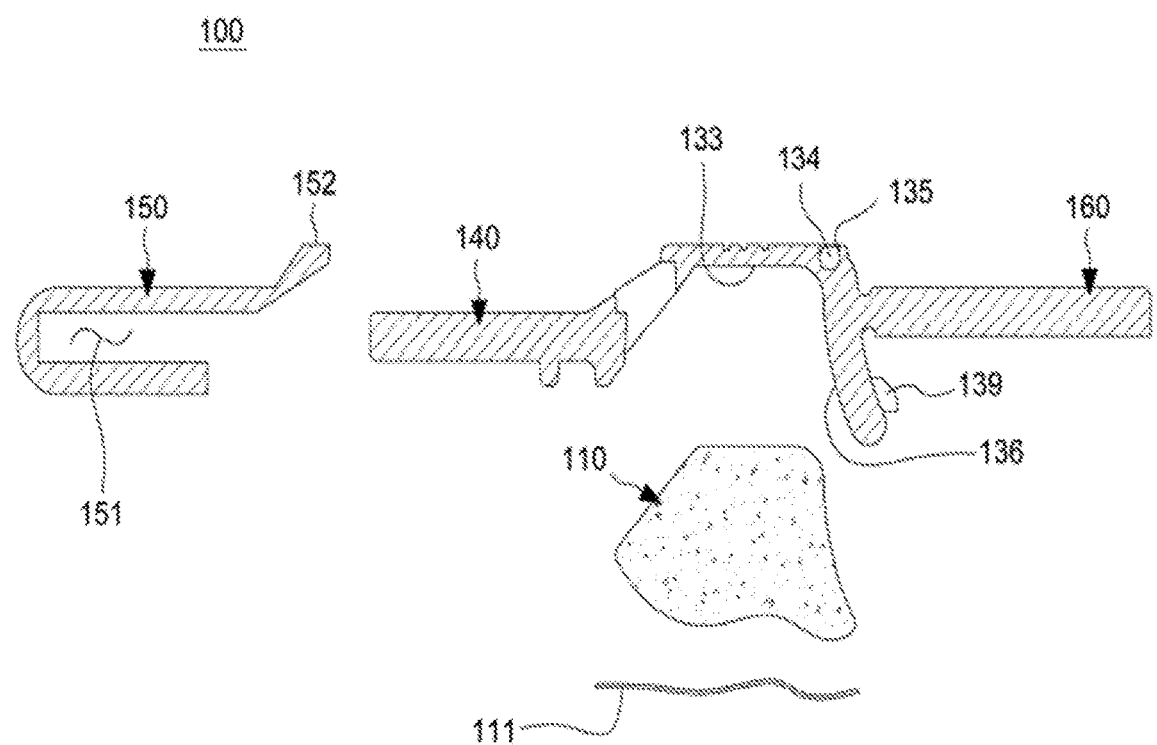
FIG. 5D is a cross-sectional view taken along line A1-A1 of FIG. 5B.
Figure 5E:
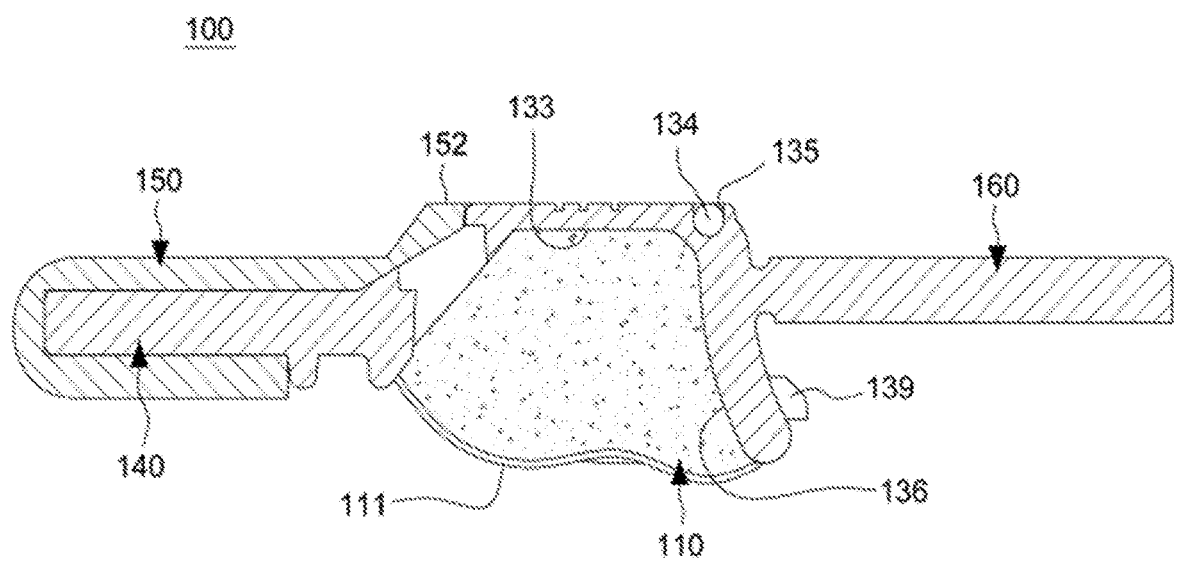
FIG. 5E is an assembled cross-sectional view of FIG. 5D.

A preliminary guide and a guide tray according to a first embodiment of the present invention will be described with reference to FIGS. 5A to 5E. FIGS. 5A and 5B are exploded perspective views of the first preferred embodiment of the preliminary guide and the guide tray for manufacturing the guide of FIG. 2 or 3 when viewed from different sides. FIG. 5C is a view looking at a grip part of the guide tray of FIG. 5A or 5B. FIG. 5D is a cross-sectional view taken along line A1-A1 of FIG. 5B. FIG. 5E is an assembled cross-sectional view of FIG. 5D.

Figure 4:
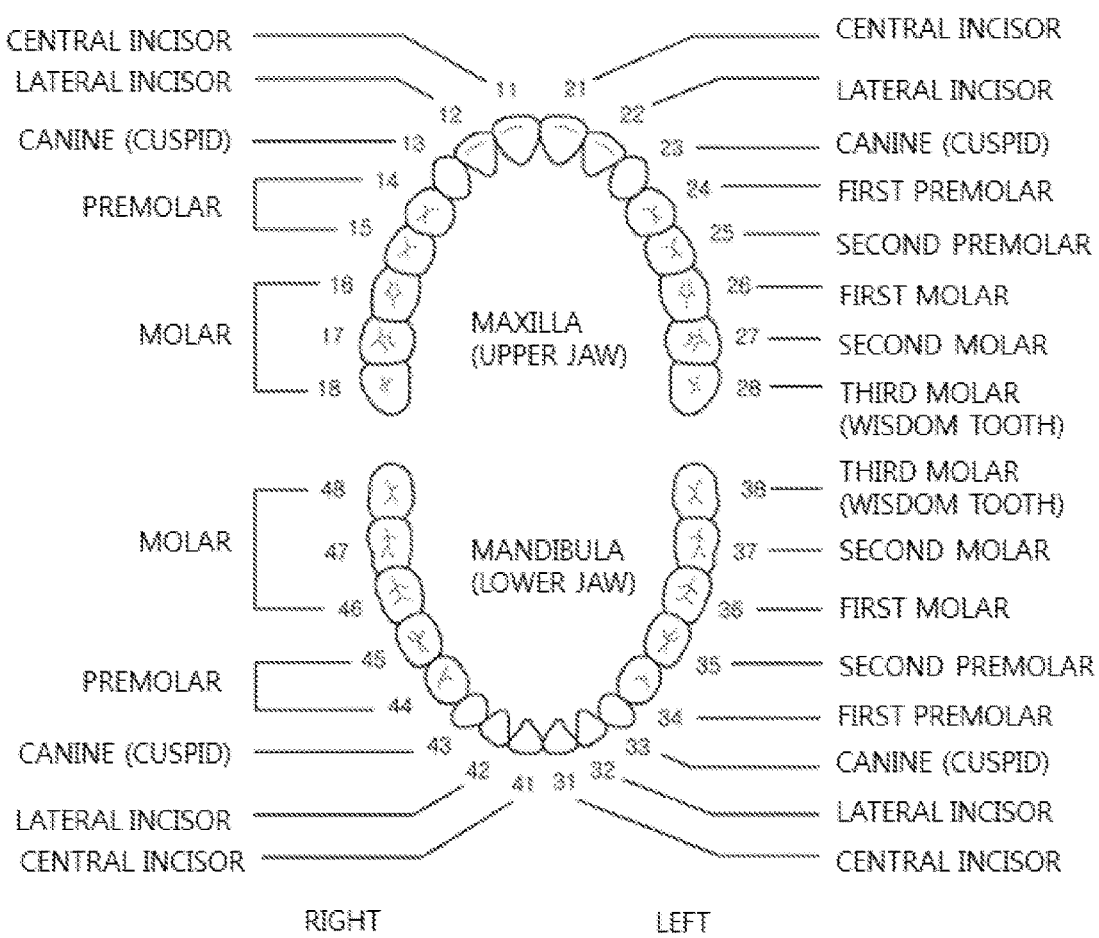
FIG. 4 is an exemplary view of a tooth structure for better understanding the description of the present invention.

The preliminary guide, which is designated by reference numeral 100, according to the first embodiment is suitably applicable when the implant placement region is concerned with upper incisors/premolars 11, 12, 13, 14, 15, 21, 22, 23, 24, and 25 in FIG. 4 or lower incisors/premolars 31, 32, 33, 34, 35, 41, 42, 43, 44, and 45 in FIG. 4.

As illustrated in FIGS. 5A to 5E, the preliminary guide 100 includes an impression resin 110 and a guide tray 120. The guide tray 120 includes an impression resin accommodation part 130, a jig fastening part 140, a protective cover part 150, and a grip part 160.

The impression resin 110 is used to mold the implant placement region in a pattern form. As the impression resin 110, a dental resin may be used that is cured naturally or artificially after use in a soft state before use. In the present invention, the dental resin has been subjected to many experiments over a long period of time so that its components and contents are optimized to better match the use of the invention. The impression resin 110 used in the present embodiment is composed of 45.27 wt % of urethane dimethacrylate, 20.0 wt % of triethylene glycol dimethacrylate, 15.1 wt % of bisphenol A-glycidyl methacrylate, 18.0 wt % of silica, 1.5 wt % of barium glass, 0.05 wt % of camphorquinone, 0.02 wt % of 2,6-ditert-butyl-4-methylphenol, and 0.06 wt % of ethyl 4-dimethylaminobenzoate.

If necessary, a curing accelerator may be added to the impression resin 110 to reduce the curing time. The curing accelerator may be added in advance before use or may be additionally added during use.

In the present invention, the exposed surface of the impression resin 110 is protected or otherwise protected as necessary. In the present embodiment, the exposed surface of the impression resin 110 is covered by a thin film 111. Thus, the exposed surface of the impression resin 110 is protected from the external environment before use, and the impression resin 110 is easily removed from the placement region since the film 111 is between the placement region and the impression resin 110 when the placement region is molded in the pattern form. In addition, even when the pattern of an undercut portion is molded in the impression resin 110, the impression resin 110 is easily removed from the placement region by the film 111 even after partial curing is performed.

The film 111 may be made of transparent or translucent vinyl having a thickness of 0.03 mm to 0.20 mm and is peeled off before the impression resin 110 is fully cured.

The impression resin accommodation part 130 is a part accommodating the impression resin 110 and has a shape corresponding to an upper incisor/premolar region or a lower incisor/premolar region which is the placement region. The impression resin accommodation part 130 may be changed in size according to the size of the placement region and applied thereto.

The impression resin accommodation part 130 has an empty space for accommodating a required amount of the impression resin 110 by connecting a first side surface 131, a bottom surface 133, and a second side surface 136 to each other. In the present embodiment, the impression resin accommodation part 130 is made of polysulfone.

The first side surface 131 is positioned inside the tooth and inclined according to the inside structure of the tooth. When the impression resin 110 is pushed into and cured in the first side surface 131, the first side surface 131 is formed with a plurality of first grooves/holes 132 spaced at intervals to securely fix the impression resin 110.

Each of the first grooves/holes 132 has a trapezoidal angled shape, and its inlet width Wi is smaller than its outlet width Wo. Due to the angled groove/hole structure, the impression resin 110 filling the first grooves/holes 132 is securely held so as not to be removed therefrom after curing. Also, even when the placement guide hole is machined to complete the guide, the impression resin 110 is securely held without being removed by mechanical drilling force. The size and shape of each of the first grooves/holes 132 may be implemented in various manners within a range that exhibits the same function depending on the characteristics of the impression resin 110.

The bottom surface 133 is positioned at the end of the tooth, and has a width about three times greater than the thickness of the tooth to accommodate tooth arrangement in various sizes and shapes.

The bottom surface 133 is provided with a plurality of matching markers 134 on the opposite surface thereof. The matching markers 134 are used to "select a preliminary guide image coinciding with the preliminary guide held by the patient and place it on the CT image having the designed placement information" in the third step of the basic manufacturing method and the sixth step of the modified manufacturing method of the present invention as described above.

Preferably, the matching markers 134 may each be made of a radiopaque material. It is preferable that at least five markers 134 are aligned at intervals to increase the accuracy of matching. They are positioned to be in a triangular shape when any three markers 134 are interconnected. Although five markers 134 are illustrated in the present embodiment, the number of markers may be decreased or increased as needed.

It is necessary to secure a sufficient clearance between the matching markers 134 and the teeth in order to improve the position identification in the CT image and the matching between the CT image and the guide tray image. Particularly, when there is a metal prosthesis, scattering may occur, resulting in interrupting the identification of the markers 134. This scattering is known to mainly occur sideways and have little effect on the upper side. In this regard, the matching markers 134 are aligned at intervals so as to be positioned above the teeth if possible.

The matching markers 134 may each be made of radiopaque metal or ceramic to be of a ball type or have a cylindrical shape. In the present embodiment, "gutta-percha", which has been widely used for other purposes in dentistry, is repurposed and used. In order to obtain a clearer CT image, each ball-type marker 134 is used and fully embedded in the groove 135 formed in the bottom surface 133 without exposing the surface thereof.

Each of the matching markers 134 has a diameter of 0.3 mm to 5.0 mm, preferably of 0.5 mm to 4.0 mm, and most preferably of 1.0 mm to 2.0 mm.

The second side surface 136 is positioned outside the tooth and is formed nearly vertically according to the outside structure of the tooth. When the impression resin 110 is pushed into and cured in the second side surface 136, the second side surface 136 is formed with a plurality of second grooves/holes 137 spaced at intervals to securely fix the impression resin 110. The second side surface 136 is further formed with a plurality of holes 138. The second grooves/holes 137 and the holes 138 have different shapes in consideration of functionality and for convenience of manufacture.

Each of the second grooves/holes 137 has a trapezoidal angled shape, and its inlet width is smaller than its outlet width similar to the first grooves/holes 132. Due to the angled groove/hole structure, the impression resin 110 filling the second grooves/holes 137 is securely held so as not to be removed therefrom after curing. Also, even when the placement guide hole is machined to complete the guide, the impression resin 110 is securely held without being removed by mechanical drilling force. The size and shape of each of the second grooves/holes 137 may be implemented in various manners within a range that exhibits the same function depending on the characteristics of the impression resin 110.

The second side surface 136 has a plurality of protruding jaws 139 formed thereon with the grip part 160 interposed therebetween, wherein the protruding jaws 139 serve to check whether the guide tray 120 is properly mounted on the working jig to complete the guide on the outer surface of the second side surface 136 or to absorb the vibration caused by mechanical drilling force when the placement guide hole is machined. The protruding jaws 139 are detachably fixed to the working jig provided in processing equipment (not illustrated). Although the protruding jaws are implemented as a means for absorbing vibration in the present embodiment, grooves recessed inwardly may also be implemented as the means.

Although the grooves/holes or holes are implemented as a means for securely fixing the impression resin in the present embodiment, the impression resin may also be securely fixed in the impression resin accommodation part using an adhesive or the like.

The jig fastening part 140 is detachably fastened to the working jig in the processing equipment when the placement guide hole is machined to complete the guide. The jig fastening part 140 is connected to the first side surface 131 and formed with two fastening holes 141.

The jig fastening part 140 is fastened to the working jig in such a manner that the fastening protrusions formed on the working jig are inserted into the fastening holes 141 and both surfaces thereof are pressed upward and downward forcefully.

The protective cover part 150 is a part for preventing a portion of the impression resin 110 from being pushed out and adhering to the jig fastening part 140 due to pressing when the implant placement region is molded in the pattern form in the impression resin 110.

The protective cover part 150 has an insertion space 151 into which the jig fastening part 140 is closely inserted and an extension 152 coming into contact with the outer surface of the first side surface 131. One side of the extension 152 is slightly raised so that the user can easily push the protective cover part 150 to the jig fastening part 140 with his/her finger. When the impression resin 110 in the impression resin accommodation part 130 is pushed out, the extension 152 can prevent the impression resin 110 from being pushed out toward the protective cover part 150.

The grip part 160 is gripped by the user's finger and connected to the outer surface of the second side surface 136. The grip part 160 may be configured to break if it is unnecessary upon use.

Although the matching markers 134 are used as the matching means in the present embodiment, a radiopaque material may be applied to the surface of the impression resin accommodation part 130, the jig fastening part 140, or the grip part 160, or they themselves may be made of a radiopaque material.

Second Embodiment

Figure 6A:
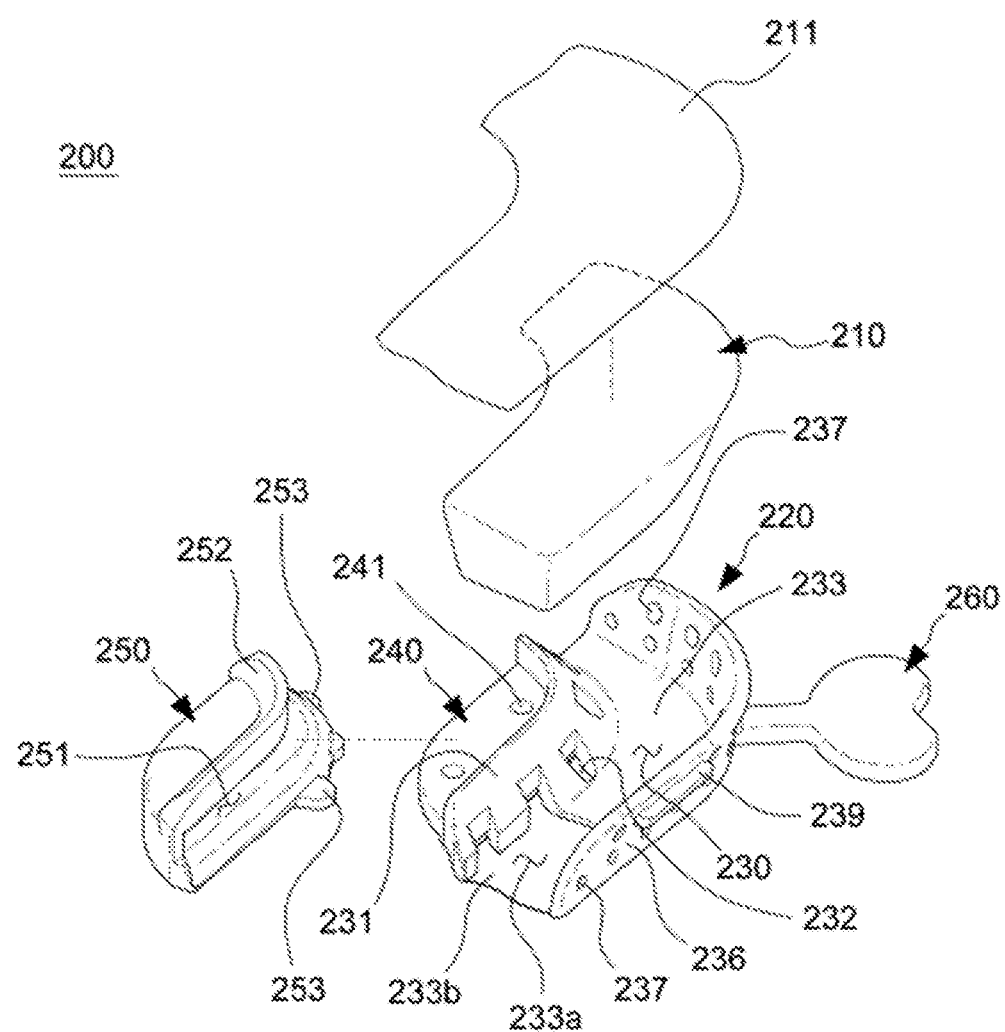
FIGS. 6A and 6B are exploded perspective views of a second preferred embodiment of a preliminary guide and a guide tray for manufacturing the guide of FIG. 2 or 3 when viewed from different sides.
Figure 6B:
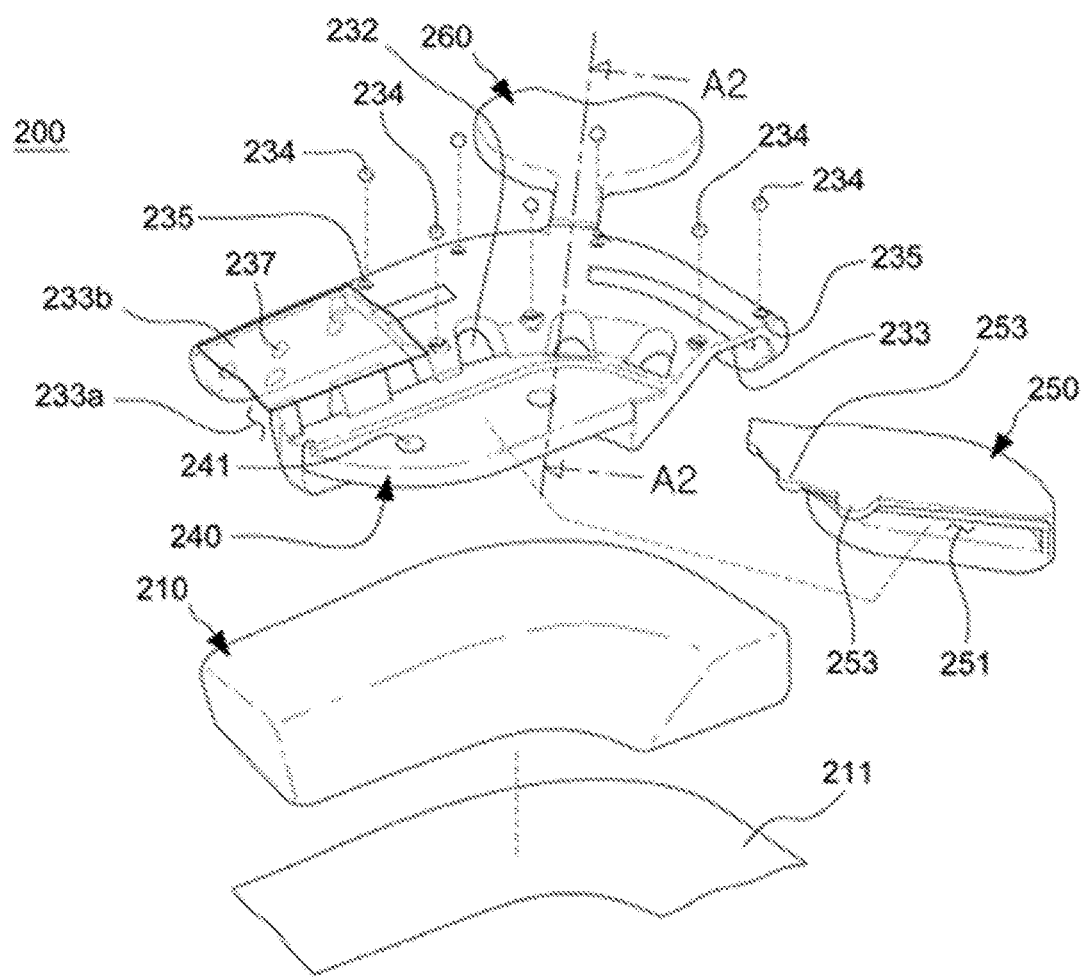
Figure 6C:
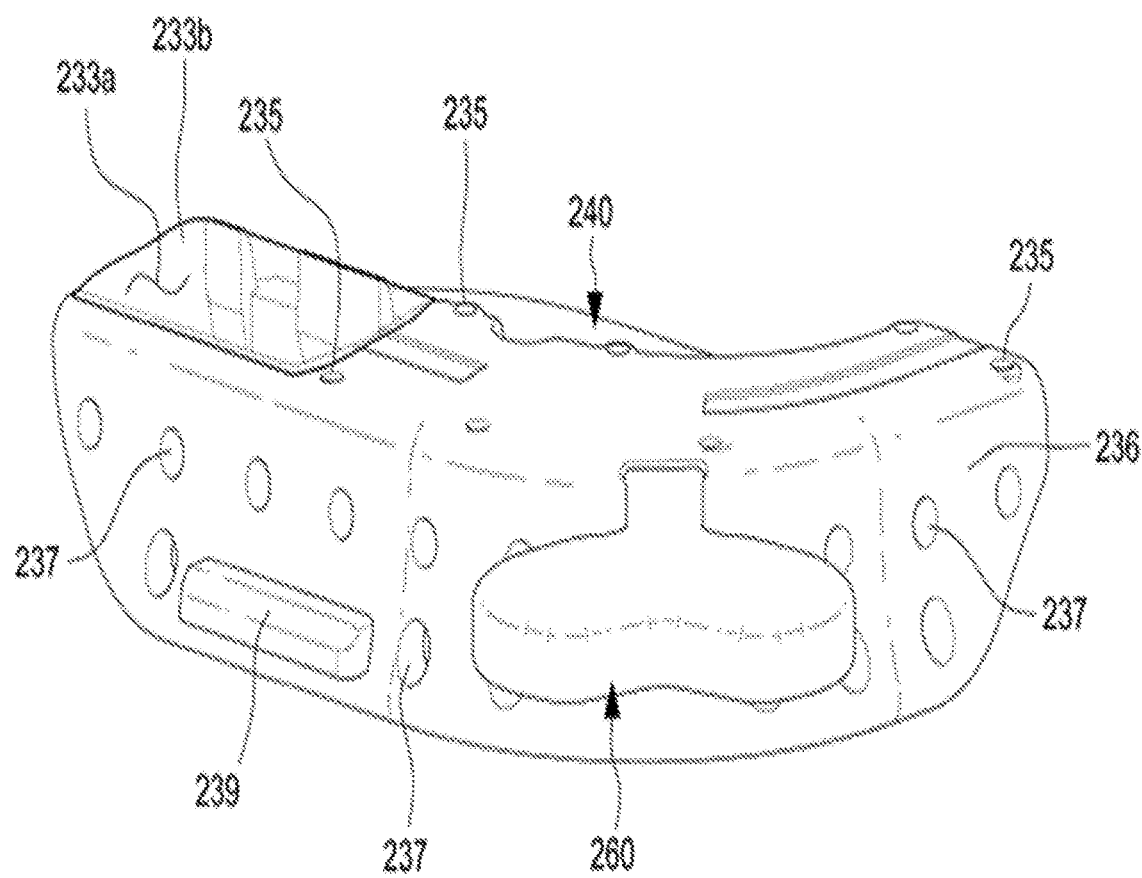
FIG. 6C is a view looking at a grip part of the guide tray of FIG. 6A or 6B.
Figure 6D:
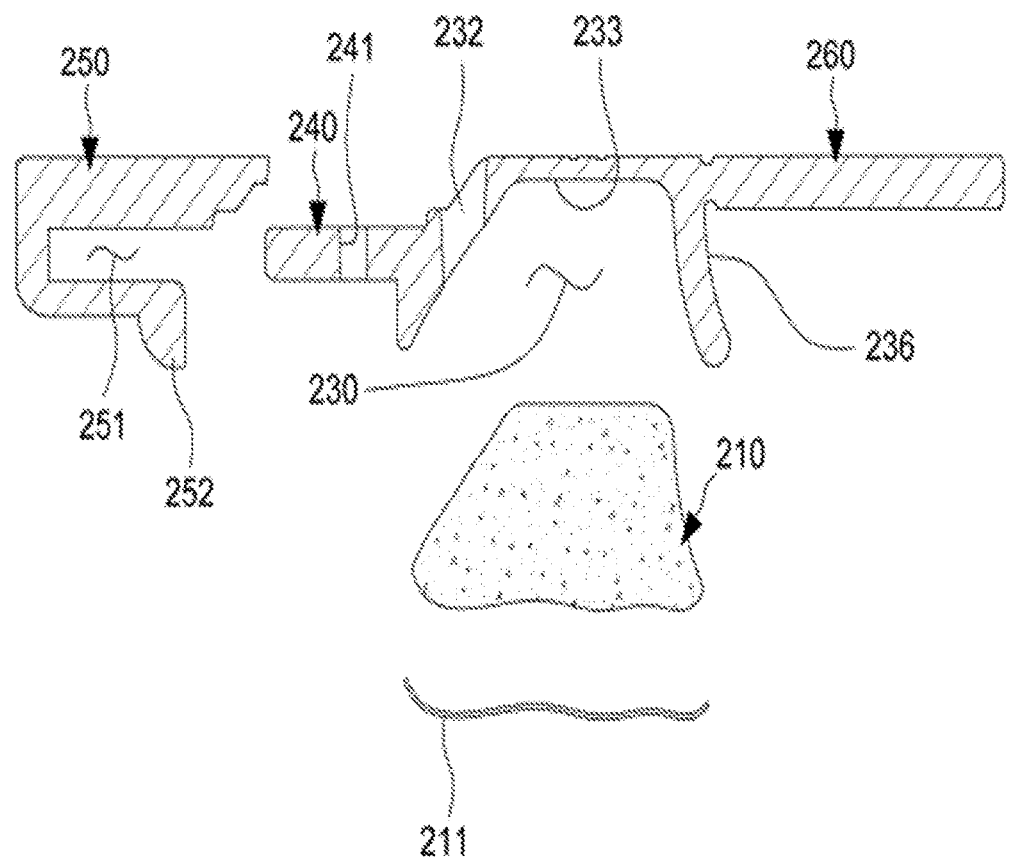
FIG. 6D is a cross-sectional view taken along line A2-A2 of FIG. 6B.
Figure 6E:
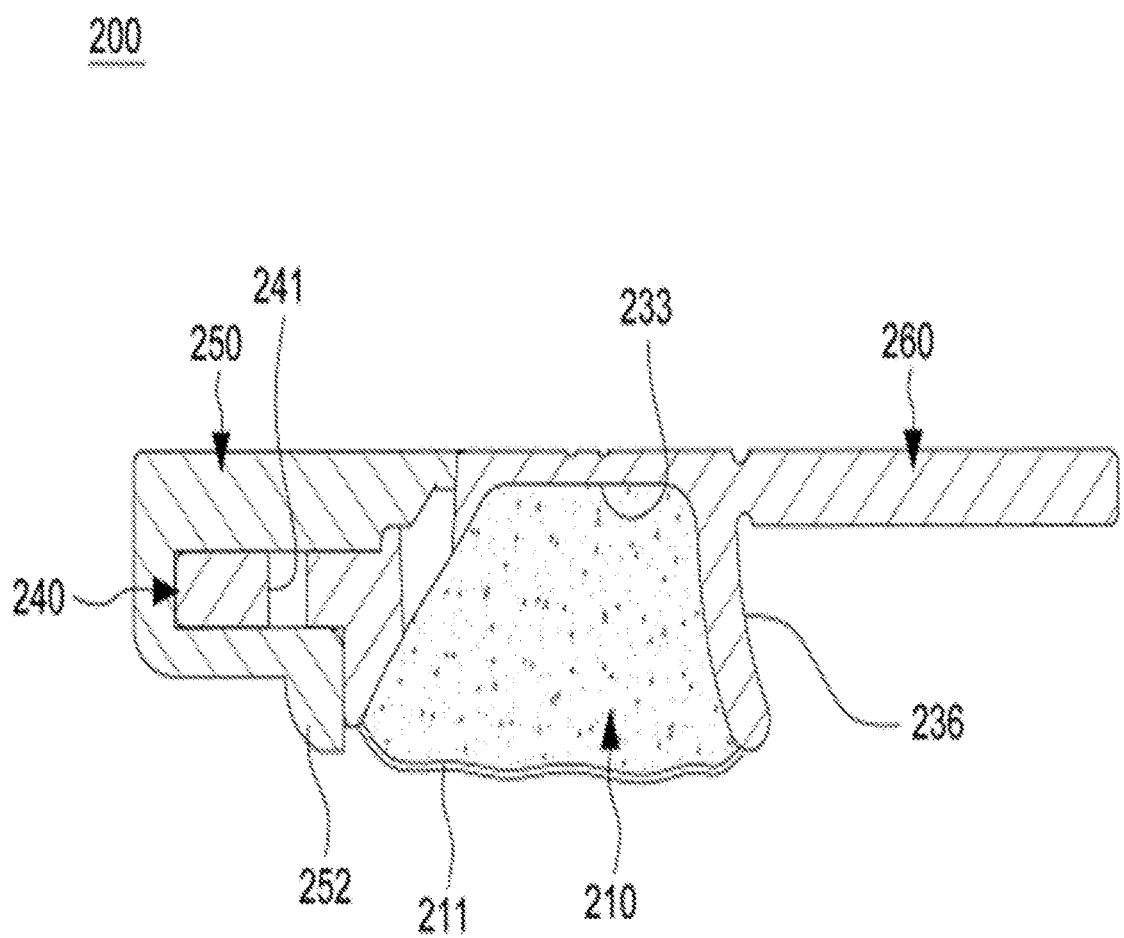
FIG. 6E is an assembled cross-sectional view of FIG. 6D.
Figure 6F:
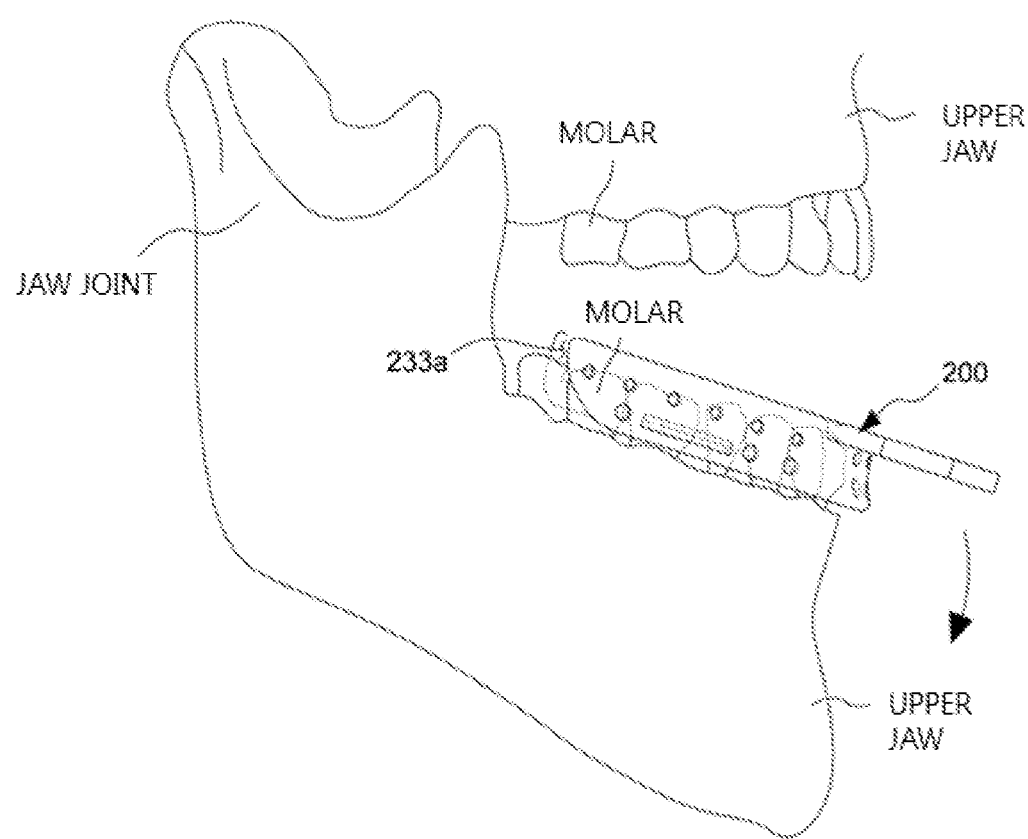
FIGS. 6F and 6G are exemplary views of a jaw structure for better understanding the description of the second embodiment.
Figure 6G:
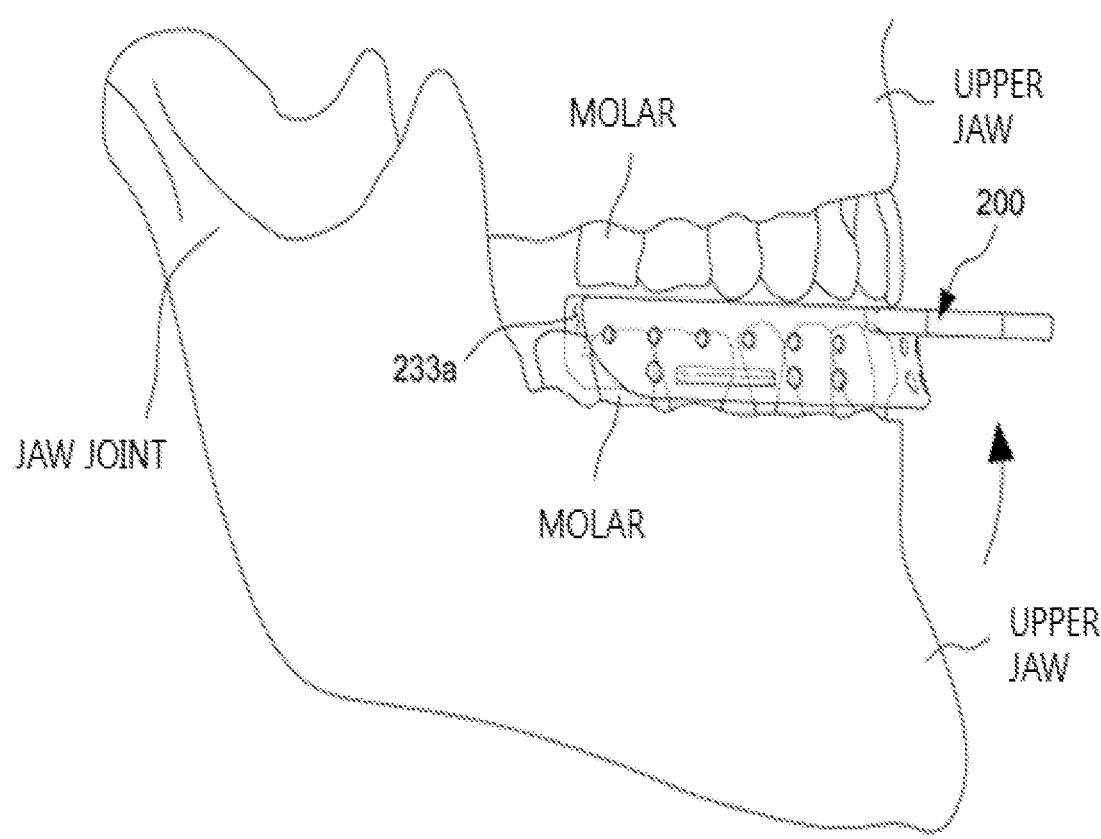

A preliminary guide and a guide tray according to a second embodiment of the present invention will be described with reference to FIGS. 6A to 6E. FIGS. 6A and 6B are exploded perspective views of the second preferred embodiment of the preliminary guide and the guide tray for manufacturing the guide of FIG. 2 or 3 when viewed from different sides. FIG. 6C is a view looking at a grip part of the guide tray of FIG. 6A or 6B. FIG. 6D is a cross-sectional view taken along line A2-A2 of FIG. 6B. FIG. 6E is an assembled cross-sectional view of FIG. 6D. FIGS. 6F and 6G are exemplary views of a jaw structure.

The preliminary guide, which is designated by reference numeral 200, according to the second embodiment is suitably applicable when the implant placement region is concerned with from an upper central incisor to an upper second molar 21, 22, 23, 24, 25, 26, and 27 in FIG. 4 and from a lower central incisor to a lower second molar 31, 32, 33, 34, 35, 36, and 37 in FIG. 4. Third molars (wisdom teeth, 28 and 38 in FIG. 4) were not considered because most patients remove them. Even when these teeth were not removed, it is unnecessary to consider them in practice because the teeth are removed during implant surgery.

As illustrated in FIGS. 6A to 6E, the preliminary guide 200 includes an impression resin 210 and a guide tray 220. The guide tray 220 includes an impression resin accommodation part 230, a jig fastening part 240, a protective cover part 250, and a grip part 260.

The impression resin 210 is used to mold the implant placement region in a pattern form. As the impression resin 210, a dental resin may be used that is cured naturally or artificially after use in a soft state before use. In the present invention, the dental resin has been subjected to many experiments over a long period of time so that its components and contents are optimized to better match the use of the invention. The impression resin 210 used in the present embodiment is composed of 45.27 wt % of urethane dimethacrylate, 20.0 wt % of triethylene glycol dimethacrylate, 15.1 wt % of bisphenol A-glycidyl methacrylate, 18.0 wt % of silica, 1.5 wt % of barium glass, 0.05 wt % of camphorquinone, 0.02 wt % of 2,6-ditert-butyl-4-methylphenol, and 0.06 wt % of ethyl 4-dimethylaminobenzoate.

If necessary, a curing accelerator may be added to the impression resin 210 to reduce the curing time. The curing accelerator may be added in advance before use or may be additionally added during use.

In the present invention, the exposed surface of the impression resin 210 is protected or otherwise protected as necessary. In the present embodiment, the exposed surface of the impression resin 210 is covered by a thin film 211. Thus, the exposed surface of the impression resin 210 is protected from the external environment before use, and the impression resin 210 is easily removed from the placement region since the film 211 is between the placement region and the impression resin 210 when the placement region is molded in the pattern form. In addition, even when the pattern of an undercut portion is molded in the impression resin 210, the impression resin 210 is easily removed from the placement region by the film 211 even after partial curing is performed.

The film 211 may be made of transparent or translucent vinyl having a thickness of 0.03 mm to 0.20 mm and is peeled off before the impression resin 210 is fully cured.

The impression resin accommodation part 230 is a part accommodating the impression resin 210 and has a shape corresponding to an upper central incisor to second molar region or a lower central incisor to second molar region which is the placement region. The impression resin accommodation part 230 may be changed in size according to the size of the placement region and applied thereto.

The impression resin accommodation part 230 has an empty space for accommodating a required amount of the impression resin 210 by connecting a first side surface 231, a bottom surface 233, and a second side surface 236 to each other. In the present embodiment, the impression resin accommodation part 230 is made of polysulfone.

The first side surface 231 is positioned inside the tooth and inclined according to the inside structure of the tooth. When the impression resin 210 is pushed into and cured in the first side surface 231, the first side surface 231 is formed with a plurality of grooves/holes 232 spaced at intervals to securely fix the impression resin 210.

Each of the grooves/holes 232 has a trapezoidal angled shape, and its inlet width is smaller than its outlet width similar to the grooves/holes 132 of FIG. 5A or 5B. Due to the angled groove/hole structure, the impression resin 210 filling the grooves/holes 232 is securely held so as not to be removed therefrom after curing. Also, even when the placement guide hole is machined to complete the guide, the impression resin 210 is securely held without being removed by mechanical drilling force. The size and shape of each of the grooves/holes 232 may be implemented in various manners within a range that exhibits the same function depending on the characteristics of the impression resin 210.

The bottom surface 233 is positioned at the end of the tooth, and has a width about three times greater than the thickness of the tooth to accommodate tooth arrangement in various sizes and shapes. Unlike the bottom surface 133 of FIG. 5A or 5B, the bottom surface 233 has an opening 233a formed at the end thereof, namely, at a portion where the molar is positioned.

In regard to the occlusion of the teeth, as illustrated in FIGS. 6F and 6G for reference, the molars inside the upper and lower jaws are first occluded by the structure in which the upper and lower jaws are opened and closed around the jaw joint.

As a result of many experiments, when the hard bottom surface 233 and the impression resin 210 are present between these molars, a space exists between teeth other than the molars so that the teeth are not normally occluded. In order to prevent such a phenomenon, the opening 233a is formed at a portion where the molars are touched or positioned in the present embodiment.

The opening 233a may be provided with a thin protective film 233b connected to the bottom surface 233 to prevent the impression resin 210 from being pushed out due to pressing by the teeth during occlusion.

The bottom surface 233 is provided with a plurality of matching markers 234 on the opposite surface thereof. The matching markers 234 are used to "select a preliminary guide image coinciding with the preliminary guide held by the patient and place it on the CT image having the designed placement information" in the third step of the basic manufacturing method and the sixth step of the modified manufacturing method of the present invention as described above.

Preferably, the matching markers 234 may each be made of a radiopaque material. It is preferable that at least five markers 234 are aligned at intervals to increase the accuracy of matching. They are positioned to be in a triangular shape when any three markers 234 are interconnected. Although six markers 234 are illustrated in the present embodiment, the number of markers may be decreased or increased as needed.

It is necessary to secure a sufficient clearance between the matching markers 234 and the teeth in order to improve the position identification in the CT image and the matching between the CT image and the guide tray image. Particularly, when there is a metal prosthesis, scattering may occur, resulting in interrupting the identification of the markers 234. This scattering is known to mainly occur sideways and have little effect on the upper side. In this regard, the matching markers 234 are aligned at intervals so as to be positioned above the teeth if possible.

The matching markers 234 may each be made of radiopaque metal or ceramic to be of a ball type or have a cylindrical shape. In the present embodiment, "gutta-percha", which has been widely used for other purposes in dentistry, is repurposed and used. In order to obtain a clearer CT image, each ball-type marker 234 is used and fully embedded in the groove 235 formed in the bottom surface 233 without exposing the surface thereof.

Each of the matching markers 234 has a diameter of 0.3 mm to 5.0 mm, preferably of 0.5 mm to 4.0 mm, and most preferably of 1.0 mm to 2.0 mm.

The second side surface 236 is positioned outside the tooth and is formed nearly vertically according to the outside structure of the tooth. When the impression resin 210 is pushed into and cured in the second side surface 236, the second side surface 236 is formed with a plurality of holes 237 spaced at intervals to securely fix the impression resin 210.

The second side surface 236 in the present embodiment differs from the second side surface 133 in the first embodiment of FIG. 5A or 5B, for convenience of manufacture or use, in that more holes 237 are formed without the grooves/holes 137. Due to such a structure, the impression resin 210 filling the holes 237 is securely held so as not to be removed therefrom after curing. Also, even when the placement guide hole is machined to complete the guide, the impression resin 210 is securely held without being removed by mechanical drilling force.

The second side surface 236 has a protruding jaw 239 formed on the side of the grip part 260, wherein the protruding jaw 239 serves to check whether the guide tray 220 is properly mounted on the working jig to complete the guide on the outer surface of the second side surface 236 or to absorb the vibration caused by mechanical drilling force when the placement guide hole is machined. The protruding jaw 239 is detachably fixed to the working jig provided in processing equipment (not illustrated). Although the protruding jaw is implemented as a means for absorbing vibration in the present embodiment, a groove recessed inwardly may also be implemented as the means.

Although the grooves/holes or holes are implemented as a means for securely fixing the impression resin in the present embodiment, the impression resin may also be securely fixed in the impression resin accommodation part using an adhesive or the like.

The jig fastening part 240 is detachably fastened to the working jig in the processing equipment when the placement guide hole is machined to complete the guide. The jig fastening part 240 is connected to the first side surface 231 and formed with two fastening holes 241.

The jig fastening part 240 is fastened to the working jig in such a manner that the fastening protrusions formed on the working jig are inserted into the fastening holes 241 and both surfaces thereof are pressed upward and downward forcefully.

The protective cover part 250 is a part for preventing a portion of the impression resin 210 from being pushed out and adhering to the jig fastening part 240 by pressing when the implant placement region is molded in the pattern form in the impression resin 210.

The protective cover part 250 has an insertion space 251 into which the jig fastening part 240 is closely inserted and an extension 252 coming into contact with the outer surface of the first side surface 231. One side of the extension 252 is slightly raised so that the user can easily push the protective cover part 250 to the jig fastening part 240 with his/her finger. When the impression resin 210 in the impression resin accommodation part 230 is pushed out, the extension 252 can prevent the impression resin 210 from being pushed out toward the protective cover part 250.

In addition, the protective cover part 250 is formed with a plurality of protrusions 253 fitted into the grooves/holes 232 in the first side surface 231. When the protrusions 253 are fitted into the grooves/holes 232, the grooves/holes 232 may not be fully filled. Hence, the impression resin 210 may be pushed into the gap between the grooves/holes.

The grip part 260 is gripped by the user's finger and connected to the outer surface of the second side surface 236. The grip part 260 may be configured to break if it is unnecessary upon use.

Although the matching markers 234 are used as the matching means in the present embodiment, a radiopaque material may be applied to the surface of the impression resin accommodation part 230, the jig fastening part 240, or the grip part 260, or they themselves may be made of a radiopaque material.

Although the illustration and description of all components are omitted by reason of redundancy, the preliminary guide 200 according to the second embodiment may be modified and embodied to have a mirror symmetrical structure. The preliminary guide in the modified embodiment having this mirror symmetric structure is suitably applicable when the implant placement region is concerned with from an upper central incisor to an upper second molar 11, 12, 13, 14, 15, 16, and 17 in FIG. 4 and from a lower central incisor to a lower second molar 41, 42, 43, 44, 45, 46, and 47 in FIG. 4. Third molars (wisdom teeth, 18 and 38 in FIG. 4) were not considered because most patients remove them. Even when these teeth were not removed, it is unnecessary to consider them in practice because the teeth are removed during implant surgery.

Third Embodiment

Figure 7A:
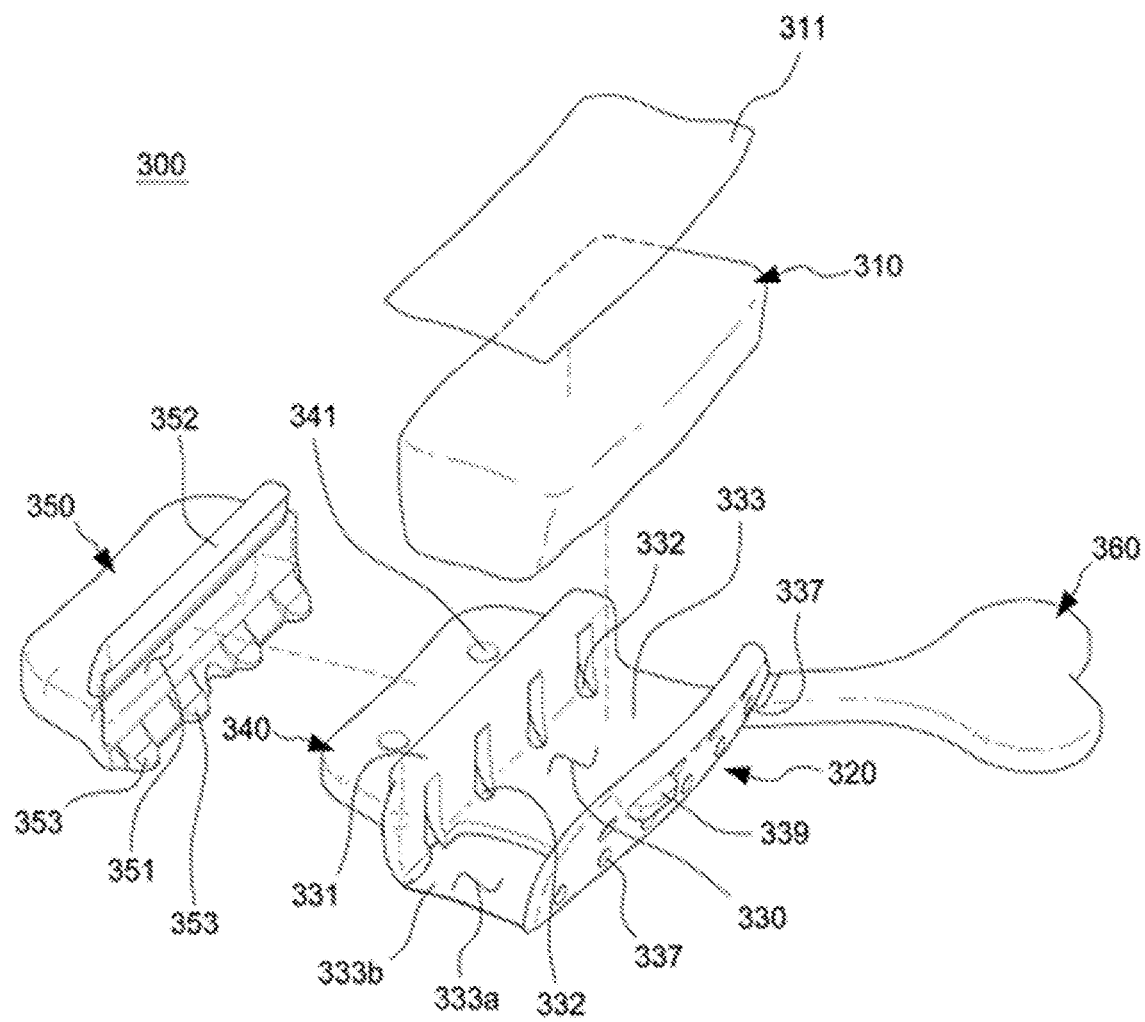
FIGS. 7A and 7B are exploded perspective views of a third preferred embodiment of a preliminary guide and a guide tray for manufacturing the guide of FIG. 2 or 3 when viewed from different sides.
Figure 7B:
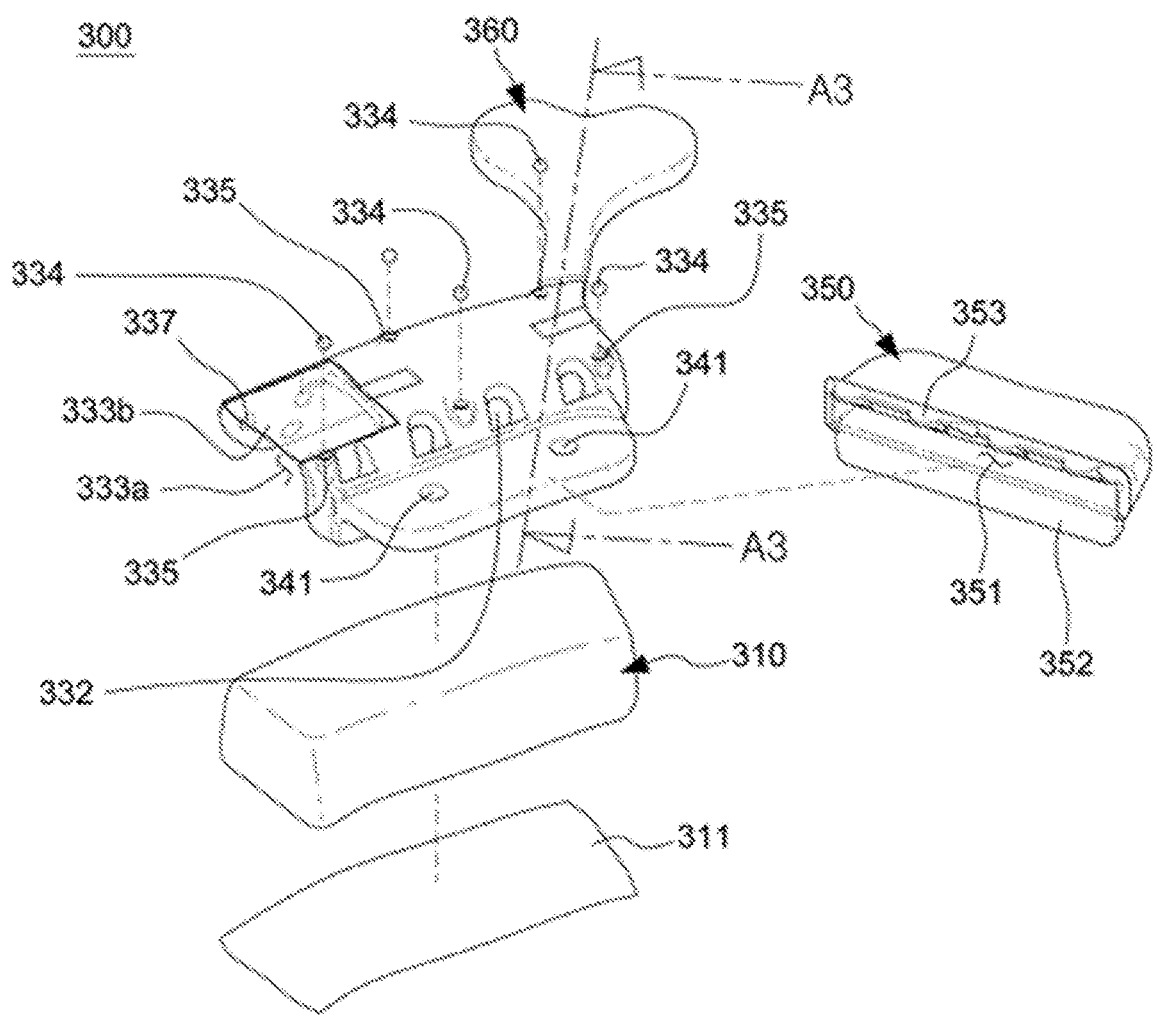
Figure 7C:
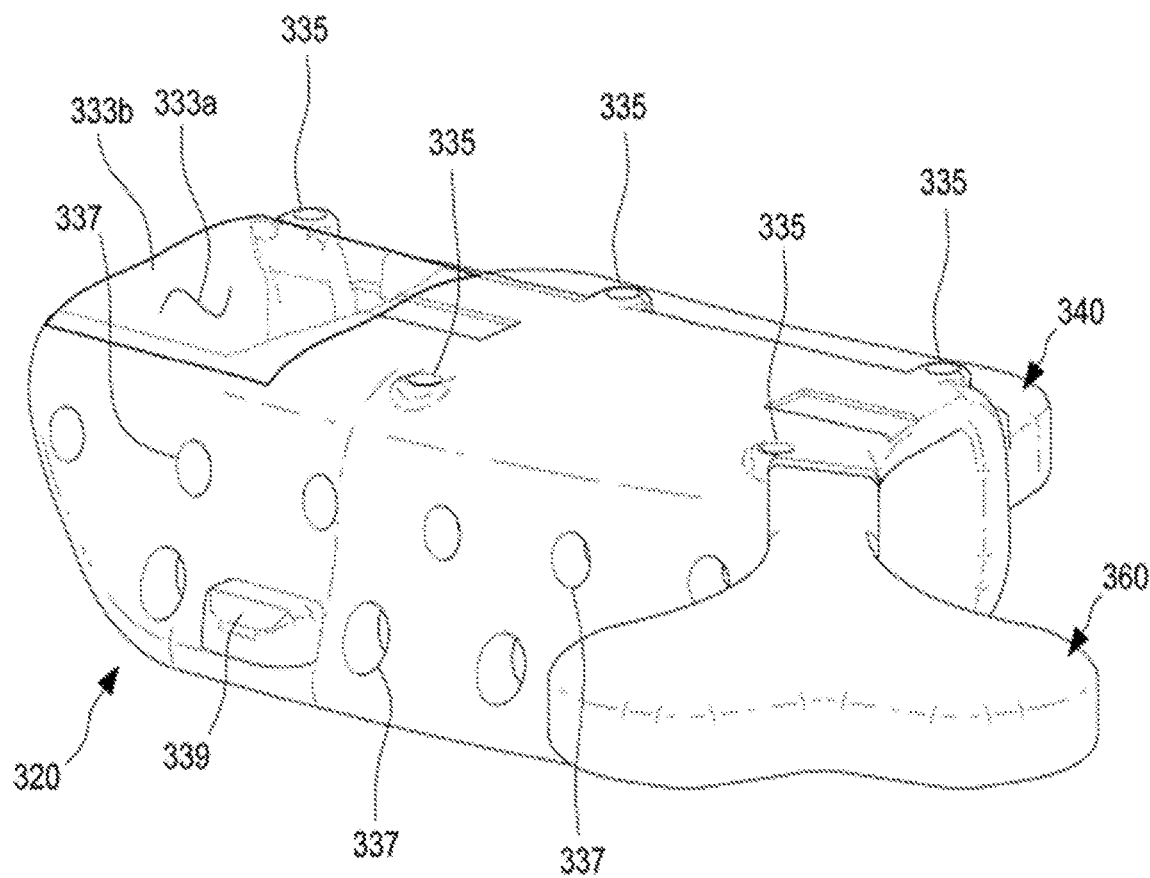
FIG. 7C is a view looking at a grip part of the guide tray of FIG. 7A or 7B.

A preliminary guide and a guide tray according to a third embodiment of the present invention will be described with reference to FIGS. 7A to 7E. FIGS. 7A and 7B are exploded perspective views of the third preferred embodiment of the preliminary guide and the guide tray for manufacturing the guide of FIG. 2 or 3 when viewed from different sides. FIG.

Figure 7D:
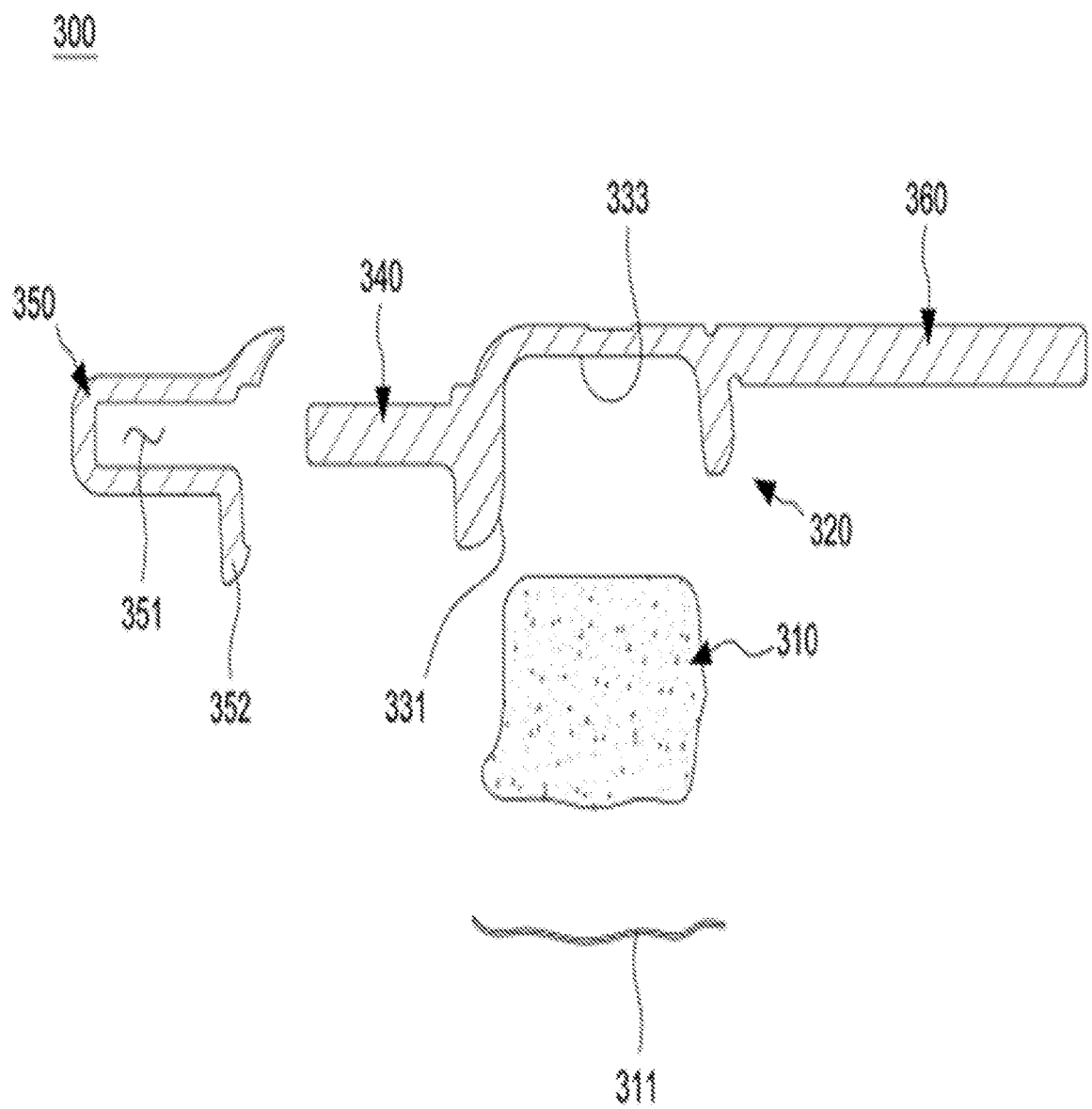
FIG. 7D is a cross-sectional view taken along line A3-A3 of FIG. 7B.
Figure 7E:
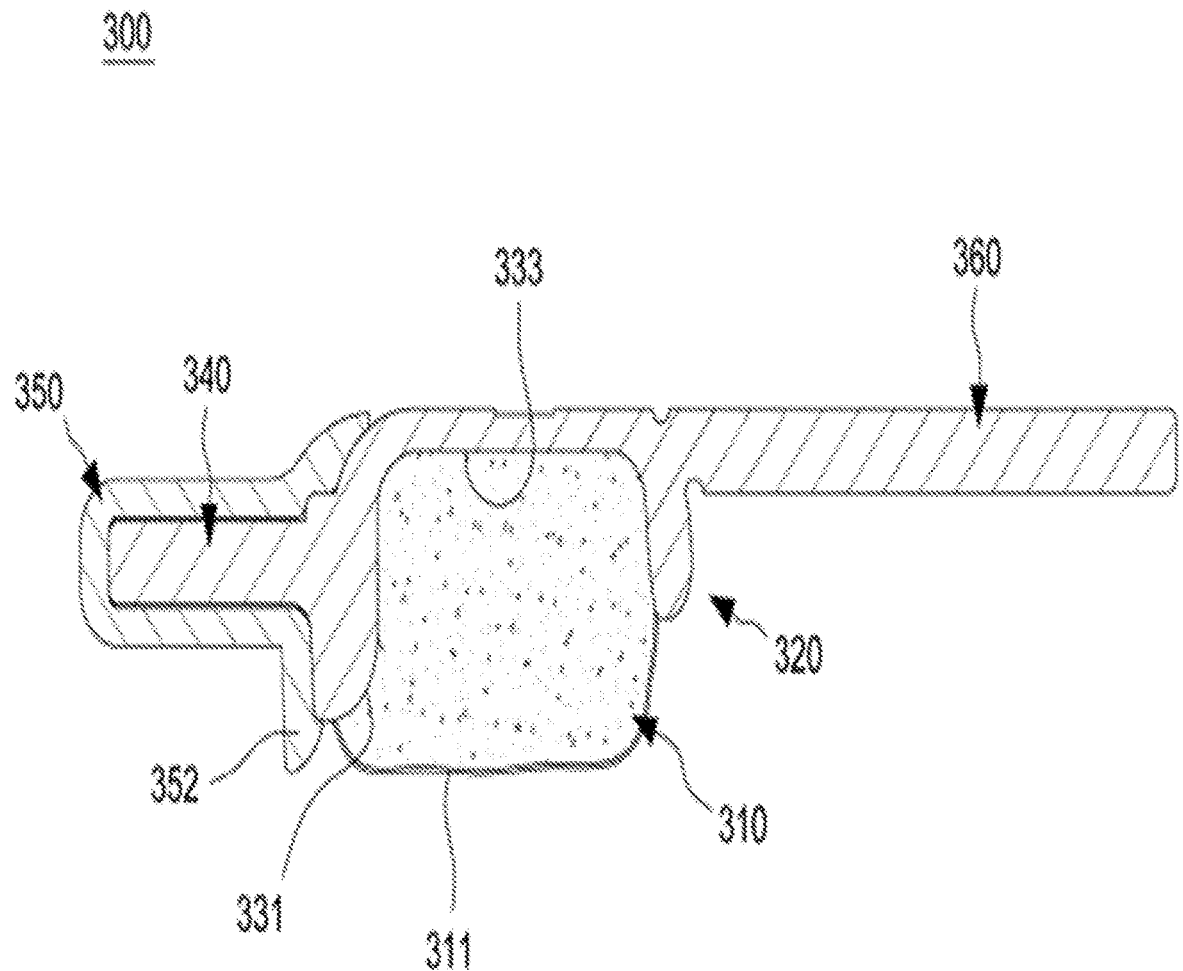
FIG. 7E is an assembled cross-sectional view of FIG. 7D.

7C is a view looking at a grip part of the guide tray of FIG. 7A or 7B. FIG. 7D is a cross-sectional view taken along line A3-A3 of FIG. 7B. FIG. 7E is an assembled cross-sectional view of FIG. 7D.

The preliminary guide, which is designated by reference numeral 300, according to the third embodiment is suitably applicable when the implant placement region is concerned with upper premolars/molars 14, 15, 16, and 17 in FIG. 4 and lower premolars/molars 34, 35, 36, and 37 in FIG. 4. Third molars (wisdom teeth, 18 and 38 in FIG. 4) were not considered because most patients remove them. Even when these teeth were not removed, it is unnecessary to consider them in practice because the teeth are removed during implant surgery.

As illustrated in FIGS. 7A to 7E, the preliminary guide 300 includes an impression resin 310 and a guide tray 320. The guide tray 320 includes an impression resin accommodation part 330, a jig fastening part 340, a protective cover part 350, and a grip part 360.

The impression resin 310 is used to mold the implant placement region in a pattern form. As the impression resin 310, a dental resin may be used that is cured naturally or artificially after use in a soft state before use. In the present invention, the dental resin has been subjected to many experiments over a long period of time so that its components and contents are optimized to better match the use of the invention. The impression resin 310 used in the present embodiment is composed of 45.27 wt % of urethane dimethacrylate, 20.0 wt % of triethylene glycol dimethacrylate, 15.1 wt % of bisphenol A-glycidyl methacrylate, 18.0 wt % of silica, 1.5 wt % of barium glass, 0.05 wt % of camphorquinone, 0.02 wt % of 2,6-ditert-butyl-4-methylphenol, and 0.06 wt % of ethyl 4-dimethylaminobenzoate.

If necessary, a curing accelerator may be added to the impression resin 310 to reduce the curing time. The curing accelerator may be added in advance before use or may be additionally added during use.

In the present invention, the exposed surface of the impression resin 310 is protected or otherwise protected as necessary. In the present embodiment, the exposed surface of the impression resin 310 is covered by a thin film 311. Thus, the exposed surface of the impression resin 310 is protected from the external environment before use, and the impression resin 310 is easily removed from the placement region since the film 311 is between the placement region and the impression resin 310 when the placement region is molded in the pattern form. In addition, even when the pattern of an undercut portion is molded in the impression resin 31, the impression resin 310 is easily removed from the placement region by the film 311 even after partial curing is performed.

The film 311 may be made of transparent or translucent vinyl having a thickness of 0.03 mm to 0.20 mm and is peeled off before the impression resin 310 is fully cured.

The impression resin accommodation part 330 is a part accommodating the impression resin 310 and has a shape corresponding to an upper premolar/molar region or a lower premolar/molar region which is the placement region. The impression resin accommodation part 330 may be changed in size according to the size of the placement region and applied thereto.

The impression resin accommodation part 330 has an empty space for accommodating a required amount of the impression resin 310 by connecting a first side surface 331, a bottom surface 333, and a second side surface 336 to each other. In the present embodiment, the impression resin accommodation part 330 is made of polysulfone.

The first side surface 331 is positioned inside the tooth and inclined according to the inside structure of the tooth. When the impression resin 310 is pushed into and cured in the first side surface 331, the first side surface 331 is formed with a plurality of grooves/holes 332 spaced at intervals to securely fix the impression resin 310.

Each of the grooves/holes 332 has a trapezoidal angled shape, and its inlet width is smaller than its outlet width similar to the grooves/holes 132 of FIG. 5A or 5B. Due to the angled groove/hole structure, the impression resin 310 filling the grooves/holes 332 is securely held so as not to be removed therefrom after curing. Also, even when the placement guide hole is machined to complete the guide, the impression resin 310 is securely held without being removed by mechanical drilling force. The size and shape of each of the grooves/holes 332 may be implemented in various manners within a range that exhibits the same function depending on the characteristics of the impression resin 310.

The bottom surface 333 is positioned at the end of the tooth, and has a width about three times greater than the thickness of the tooth to accommodate tooth arrangement in various sizes and shapes. Similar to the bottom surface 233 of FIG. 6A or 6B, the bottom surface 333 has an opening 333a formed at the end thereof, namely, at a portion where the molar is positioned. Since the reason is the same as that described in the second embodiment, a detailed description thereof will be omitted.

The opening 333a may be provided with a thin protective film 333b connected to the bottom surface 333 to prevent the impression resin 310 from being pushed out due to pressing by the teeth during occlusion.

The bottom surface 333 is provided with a plurality of matching markers 334 on the opposite surface thereof. The matching markers 334 are used to "select a preliminary guide image coinciding with the preliminary guide held by the patient and place it on the CT image having the designed placement information" in the third step of the basic manufacturing method and the sixth step of the modified manufacturing method of the present invention as described above.

Preferably, the matching markers 334 may each be made of a radiopaque material. It is preferable that at least five markers 334 are aligned at intervals to increase the accuracy of matching. They are positioned to be in a triangular shape when any three markers 334 are interconnected. Although five markers 334 are illustrated in the present embodiment, the number of markers may be decreased or increased as needed.

It is necessary to secure a sufficient clearance between the matching markers 334 and the teeth in order to improve the position identification in the CT image and the matching between the CT image and the guide tray image. Particularly, when there is a metal prosthesis, scattering may occur, resulting in interrupting the identification of the markers 334. This scattering is known to mainly occur sideways and have little effect on the upper side. In this regard, the matching markers 334 are aligned at intervals so as to be positioned above the teeth if possible.

The matching markers 334 may each be made of radiopaque metal or ceramic to be of a ball type or have a cylindrical shape. In the present embodiment, "gutta-percha", which has been widely used for other purposes in dentistry, is repurposed and used. In order to obtain a clearer CT image, each ball-type marker 334 is used and fully embedded in the groove 335 formed in the bottom surface 333 without exposing the surface thereof.

Each of the matching markers 334 has a diameter of 0.3 mm to 5.0 mm, preferably of 0.5 mm to 4.0 mm, and most preferably of 1.0 mm to 2.0 mm.

The second side surface 336 is positioned outside the tooth and is formed nearly vertically according to the outside structure of the tooth. When the impression resin 310 is pushed into and cured in the second side surface 336, the second side surface 336 is formed with a plurality of holes 337 spaced at intervals to securely fix the impression resin 310.

The second side surface 336 in the present embodiment is formed with more holes 337 for convenience of manufacture or use, similar to the second side surface 233 in the second embodiment of FIG. 6A or 6B. Due to such a structure, the impression resin 310 filling the holes 337 is securely held so as not to be removed therefrom after curing. Also, even when the placement guide hole is machined to complete the guide, the impression resin 310 is securely held without being removed by mechanical drilling force.

The second side surface 336 has a protruding jaw 339 formed on the side of the grip part 360, wherein the protruding jaw 339 serves to check whether the guide tray 320 is properly mounted on the working jig to complete the guide on the outer surface of the second side surface 336 or to absorb the vibration caused by mechanical drilling force when the placement guide hole is machined. The protruding jaw 339 is detachably fixed to the working jig provided in processing equipment (not illustrated). Although the protruding jaw is implemented as a means for absorbing vibration in the present embodiment, a groove recessed inwardly may also be implemented as the means.

Although the matching markers 334 are used as the matching means in the present embodiment, a radiopaque material may be applied to the surface of the impression resin accommodation part 330, or the impression resin accommodation part 330 itself may be made of a radiopaque material.

Although the grooves/holes or holes are implemented as a means for securely fixing the impression resin in the present embodiment, the impression resin may also be securely fixed in the impression resin accommodation part using an adhesive or the like.

The jig fastening part 340 is detachably fastened to the working jig in the processing equipment when the placement guide hole is machined to complete the guide. The jig fastening part 340 is connected to the first side surface 331 and formed with two fastening holes 341.

The jig fastening part 340 is fastened to the working jig in such a manner that the fastening protrusions formed on the working jig are inserted into the fastening holes 341 and both surfaces thereof are pressed upward and downward forcefully.

The protective cover part 350 is a part for preventing a portion of the impression resin 310 from being pushed out and adhering to the jig fastening part 340 by pressing when the implant placement region is molded in the pattern form in the impression resin 310.

The protective cover part 350 has an insertion space 351 into which the jig fastening part 340 is closely inserted and an extension 352 coming into contact with the outer surface of the first side surface 331. One side of the extension 352 is slightly raised so that the user can easily push the protective cover part 350 to the jig fastening part 340 with his/her finger. When the impression resin 310 in the impression resin accommodation part 330 is pushed out, the extension 352 can prevent the impression resin 310 from being pushed out toward the protective cover part 350.

In addition, the protective cover part 350 is formed with a plurality of protrusions 353 fitted into the grooves/holes 332 in the first side surface 331. When the protrusions 353 are fitted into the grooves/holes 332, the grooves/holes 332 may not be fully filled. Hence, the impression resin 310 may be pushed into the gap between the grooves/holes.

The grip part 360 is gripped by the user's finger and connected to the outer surface of the second side surface 336. The grip part 360 may be configured to break if it is unnecessary upon use.

Although the matching markers 334 are used as the matching means in the present embodiment, a radiopaque material may be applied to the surface of the impression resin accommodation part 330, the jig fastening part 340, or the grip part 360, or they themselves may be made of a radiopaque material.

Although the illustration and description of all components are omitted by reason of redundancy, the preliminary guide 300 according to the third embodiment may be modified and embodied to have a mirror symmetrical structure. The preliminary guide in the modified embodiment having this mirror symmetric structure is suitably applicable when the implant placement region is concerned with upper premolars/molars 24, 25, 26, and 27 in FIG. 4 and from lower premolars/molars 44, 45, 46, and 47 in FIG. 4. Third molars (wisdom teeth, 28 and 48 in FIG. 4) were not considered because most patients remove them. Even when these teeth were not removed, it is unnecessary to consider them in practice because the teeth are removed during implant surgery.

Fourth Embodiment

Figure 8A:
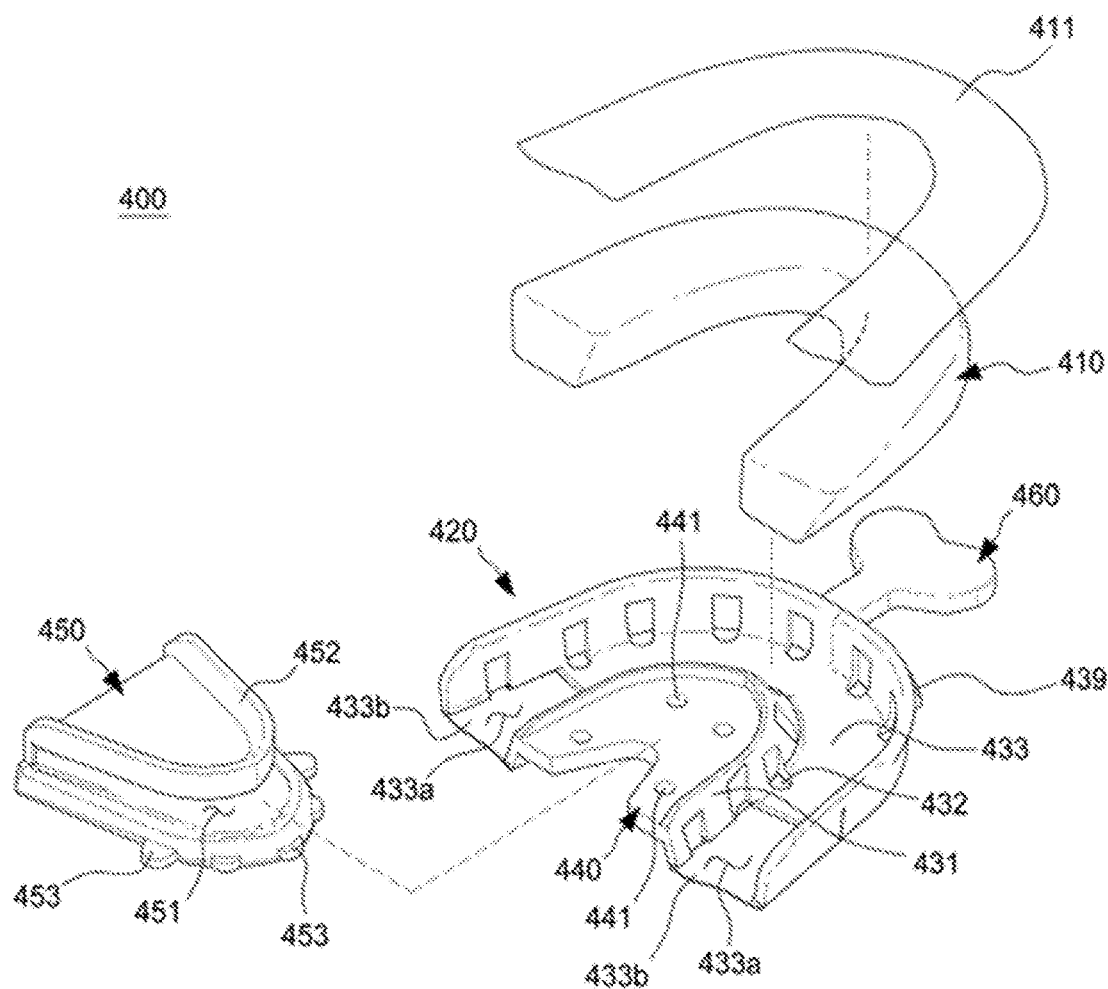
FIGS. 8A and 8B are exploded perspective views of a fourth preferred embodiment of a preliminary guide and a guide tray for manufacturing the guide of FIG. 2 or 3 when viewed from different sides.
Figure 8B:
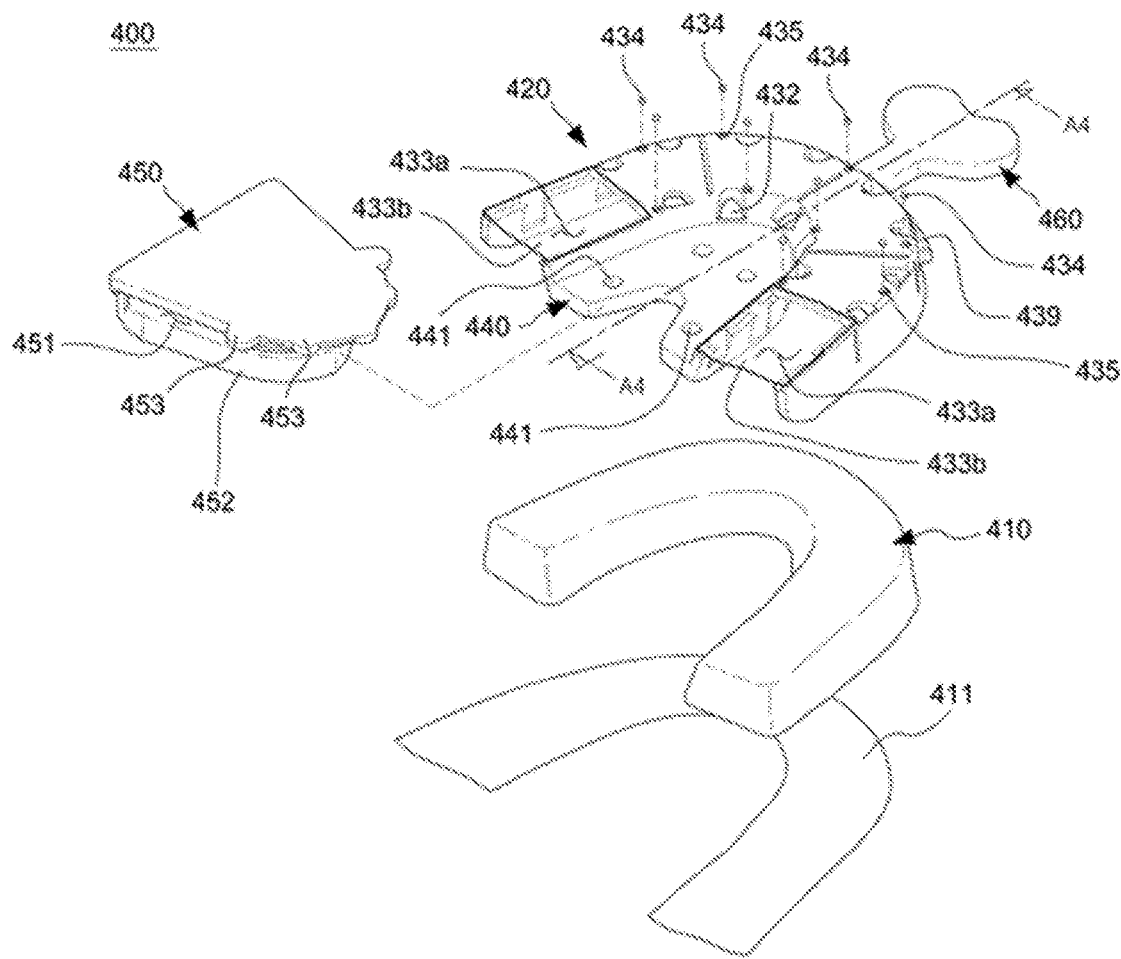
Figure 8C:
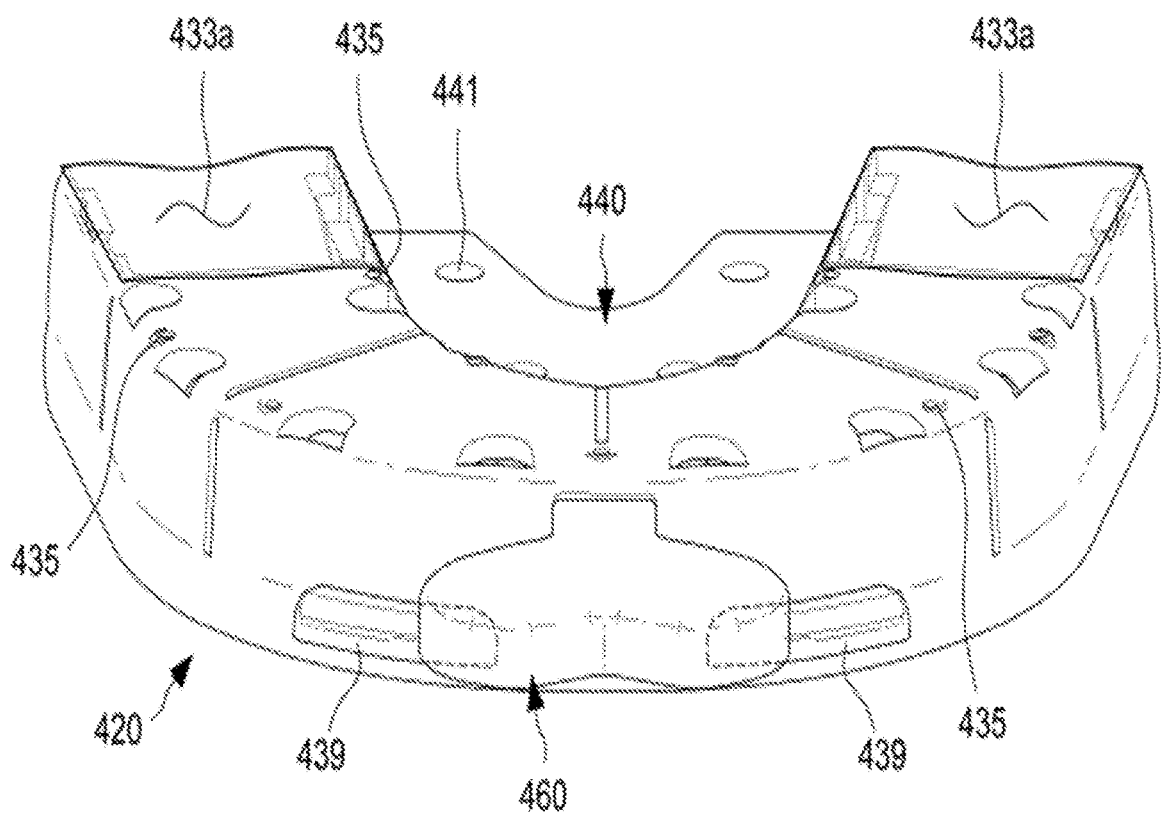
FIG. 8C is a view looking at a grip part of the guide tray of FIG. 8A or 8B.
Figure 8D:
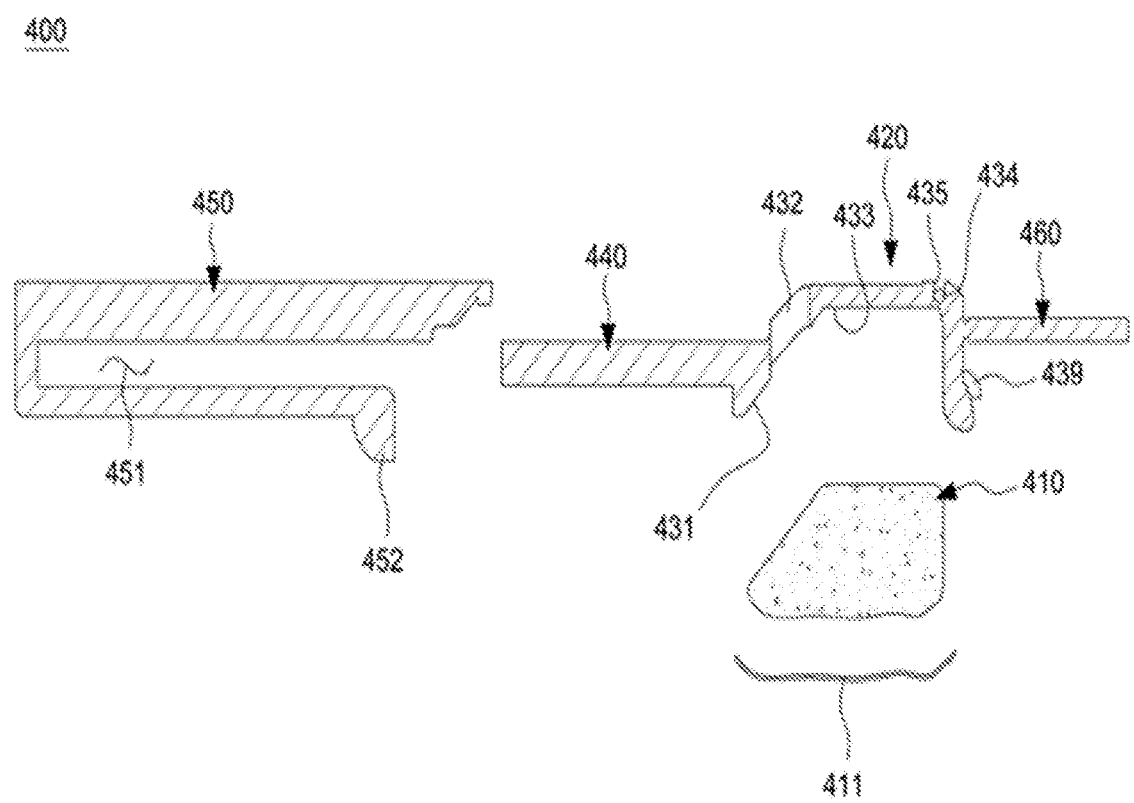
FIG. 8D is a cross-sectional view taken along line A4-A4 of FIG. 8B.
Figure 8E:
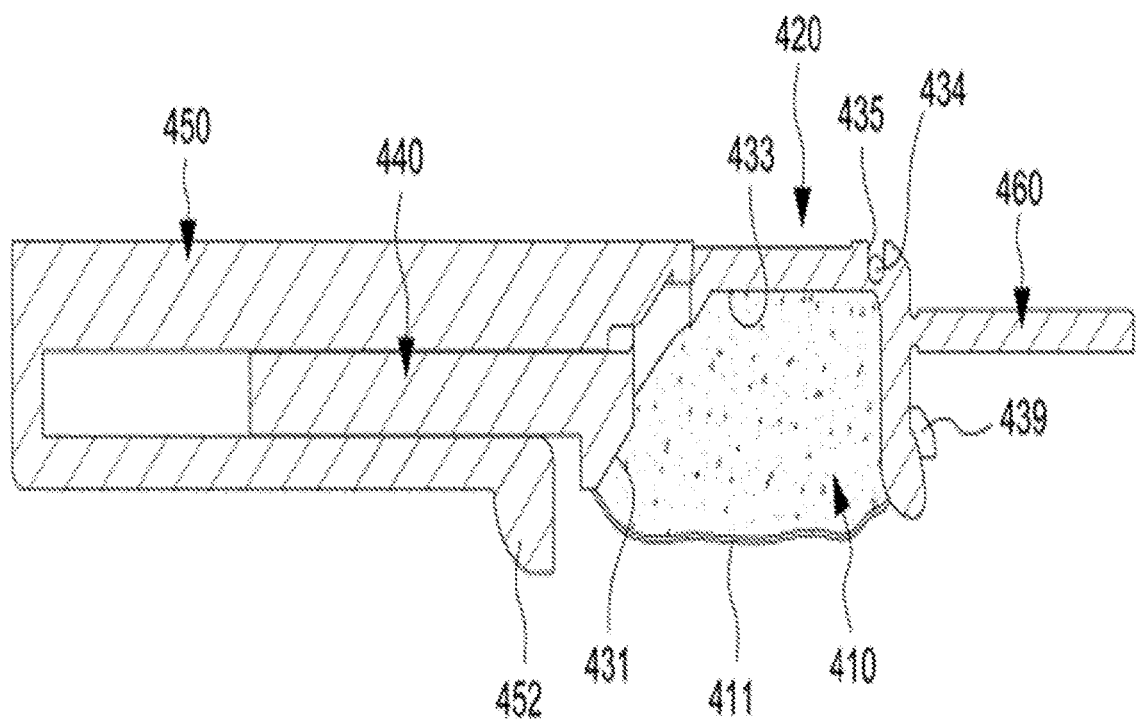
FIG. 8E is an assembled cross-sectional view of FIG. 8D.

A preliminary guide and a guide tray according to a fourth embodiment of the present invention will be described with reference to FIGS. 8A to 8E. FIGS. 8A and 8B are exploded perspective views of the fourth preferred embodiment of the preliminary guide and the guide tray for manufacturing the guide of FIG. 2 or 3 when viewed from different sides. FIG. 8C is a view looking at a grip part of the guide tray of FIG. 8A or 8B. FIG. 8D is a cross-sectional view taken along line A4-A4 of FIG. 8B. FIG. 8E is an assembled cross-sectional view of FIG. 8D.

The preliminary guide, which is designated by reference numeral 400, according to the fourth embodiment is suitably applicable when the implant placement region is concerned with from an upper central incisor to an upper second molar 11, 12, 13, 14, 15, 16, 17, 21, 22, 23, 24, 25, 26, and 27 in FIG. 4 and from a lower central incisor to a lower second molar 31, 32, 33, 34, 35, 36, 37, 41, 42, 43, 44, 45, 46, and 47 in FIG. 4.

As illustrated in FIGS. 8A to 8E, the preliminary guide 400 includes an impression resin 410 and a guide tray 420. The guide tray 420 includes an impression resin accommodation part 430, a jig fastening part 440, a protective cover part 450, and a grip part 460.

The impression resin 410 is used to mold the implant placement region in a pattern form. As the impression resin 410, a dental resin may be used that is cured naturally or artificially after use in a soft state before use. In the present invention, the dental resin has been subjected to many experiments over a long period of time so that its components and contents are optimized to better match the use of the invention. The impression resin 410 used in the present embodiment is composed of 45.27 wt % of urethane dimethacrylate, 20.0 wt % of triethylene glycol dimethacrylate, 15.1 wt % of bisphenol A-glycidyl methacrylate, 18.0 wt % of silica, 1.5 wt % of barium glass, 0.05 wt % of camphorquinone, 0.02 wt % of 2,6-ditert-butyl-4-methylphenol, and 0.06 wt % of ethyl 4-dimethylaminobenzoate.

If necessary, a curing accelerator may be added to the impression resin 410 to reduce the curing time. The curing accelerator may be added in advance before use or may be additionally added during use.

In the present invention, the exposed surface of the impression resin 410 is protected or otherwise protected as necessary. In the present embodiment, the exposed surface of the impression resin 410 is covered by a thin film 411. Thus, the exposed surface of the impression resin 410 is protected from the external environment before use, and the impression resin 410 is easily removed from the placement region since the film 411 is between the placement region and the impression resin 410 when the placement region is molded in the pattern form. In addition, even when the pattern of an undercut portion is molded in the impression resin 410, the impression resin 410 is easily removed from the placement region by the film 411 even after partial curing is performed.

The film 411 may be made of transparent or translucent vinyl having a thickness of 0.03 mm to 0.20 mm and is peeled off before the impression resin 410 is fully cured.

The impression resin accommodation part 430 is a part accommodating the impression resin 410 and has a shape corresponding to an upper central incisor to second molar region or a lower central incisor to second molar region which is the placement region. The impression resin accommodation part 430 may be changed in size according to the size of the placement region and applied thereto.

The impression resin accommodation part 430 has an empty space for accommodating a required amount of the impression resin 410 by connecting a first side surface 431, a bottom surface 433, and a second side surface 436 to each other. In the present embodiment, the impression resin accommodation part 430 is made of polysulfone.

The first side surface 431 is positioned inside the tooth and inclined according to the inside structure of the tooth. When the impression resin 410 is pushed into and cured in the first side surface 431, the first side surface 431 is formed with a plurality of first grooves/holes 432 spaced at intervals to securely fix the impression resin 410.

Each of the first grooves/holes 432 has a trapezoidal angled shape, and its inlet width is smaller than its outlet width similar to the first grooves/holes 132 of FIG. 5A or 5B. Due to the angled groove/hole structure, the impression resin 410 filling the first grooves/holes 432 is securely held so as not to be removed therefrom after curing. Also, even when the placement guide hole is machined to complete the guide, the impression resin 410 is securely held without being removed by mechanical drilling force. The size and shape of each of the first grooves/holes 432 may be implemented in various manners within a range that exhibits the same function depending on the characteristics of the impression resin 410.

The bottom surface 433 is positioned at the end of the tooth, and has a width about three times greater than the thickness of the tooth to accommodate tooth arrangement in various sizes and shapes. Similar to the bottom surface 233 of FIG. 6A or 6B, the bottom surface 433 has an opening 433*a* formed at the end thereof, namely, at a portion where the molar is positioned. Since the reason is the same as that described in the second embodiment, a detailed description thereof will be omitted.

The opening 433*a* may be provided with a thin protective film 433*b* connected to the bottom surface 433 to prevent the impression resin 410 from being pushed out due to pressing by the teeth during occlusion.

The bottom surface 433 is provided with a plurality of matching markers 434 on the opposite surface thereof. The matching markers 434 are used to "select a preliminary guide image coinciding with the preliminary guide held by the patient and place it on the CT image having the designed placement information" in the third step of the basic manufacturing method and the sixth step of the modified manufacturing method of the present invention as described above.

Preferably, the matching markers 434 may each be made of a radiopaque material. It is preferable that at least five markers 434 are aligned at intervals to increase the accuracy of matching. They are positioned to be in a triangular shape when any three markers 434 are interconnected. Although nine markers 434 are illustrated in the present embodiment, the number of markers may be decreased or increased as needed.

It is necessary to secure a sufficient clearance between the matching markers 434 and the teeth in order to improve the position identification in the CT image and the matching between the CT image and the guide tray image. Particularly, when there is a metal prosthesis, scattering may occur, resulting in interrupting the identification of the markers 434. This scattering is known to mainly occur sideways and have little effect on the upper side. In this regard, the matching markers 434 are aligned at intervals so as to be positioned above the teeth if possible.

The matching markers 434 may each be made of radiopaque metal or ceramic to be of a ball type or have a cylindrical shape. In the present embodiment, "gutta-percha", which has been widely used for other purposes in dentistry, is repurposed and used. In order to obtain a clearer CT image, each ball-type marker 434 is used and fully embedded in the groove 435 formed in the bottom surface 433 without exposing the surface thereof.

Each of the matching markers 434 has a diameter of 0.3 mm to 5.0 mm, preferably of 0.5 mm to 4.0 mm, and most preferably of 1.0 mm to 2.0 mm.

The second side surface 436 is positioned outside the tooth and is formed nearly vertically according to the outside structure of the tooth. When the impression resin 410 is pushed into and cured in the second side surface 436, the second side surface 436 is formed with a plurality of second grooves/holes 437 spaced at intervals to securely fix the impression resin 410.

Each of the second grooves/holes 437 has a trapezoidal angled shape, and its inlet width is smaller than its outlet width similar the first grooves/holes 432. Due to the angled groove/hole structure, the impression resin 410 filling the second grooves/holes 437 is securely held so as not to be removed therefrom after curing. Also, even when the placement guide hole is machined to complete the guide, the impression resin 410 is securely held without being removed by mechanical drilling force. The size and shape of each of the second grooves/holes 437 may be implemented in various manners within a range that exhibits the same function depending on the characteristics of the impression resin 410.

The second side surface 436 has a plurality of protruding jaws 439 formed thereon with the grip part 460 interposed therebetween, wherein the protruding jaws 439 serve to check whether the guide tray 420 is properly mounted on the working jig to complete the guide on the outer surface of the second side surface 436 or to absorb the vibration caused by mechanical drilling force when the placement guide hole is machined. The protruding jaws 439 are detachably fixed to the working jig provided in processing equipment (not illustrated). Although the protruding jaws are implemented as a means for absorbing vibration in the present embodiment, grooves recessed inwardly may also be implemented as the means.

Although the matching markers 434 are used as the matching means in the present embodiment, a radiopaque material may be applied to the surface of the impression resin accommodation part 430, or the impression resin accommodation part 430 itself may be made of a radiopaque material.

Although the grooves/holes or holes are implemented as a means for securely fixing the impression resin in the present embodiment, the impression resin may also be securely fixed in the impression resin accommodation part using an adhesive or the like.

The jig fastening part 440 is detachably fastened to the working jig in the processing equipment when the placement guide hole is machined to complete the guide. The jig fastening part 440 is connected to the first side surface 431 and formed with two fastening holes 441.

The jig fastening part 440 is fastened to the working jig in such a manner that the fastening protrusions formed on the working jig are inserted into the fastening holes 441 and both surfaces thereof are pressed upward and downward forcefully.

The protective cover part 450 is a part for preventing a portion of the impression resin 410 from being pushed out and adhering to the jig fastening part 440 by pressing when the implant placement region is molded in the pattern form in the impression resin 410.

The protective cover part 450 has an insertion space 451 into which the jig fastening part 440 is closely inserted and an extension 452 coming into contact with the outer surface of the first side surface 431. One side of the extension 452 is slightly raised so that the user can easily push the protective cover part 450 to the jig fastening part 440 with his/her finger. When the impression resin 410 in the impression resin accommodation part 430 is pushed out, the extension 452 can prevent the impression resin 410 from being pushed out toward the protective cover part 450.

The grip part 460 is gripped by the user's finger and connected to the outer surface of the second side surface 436. The grip part 460 may be configured to break if it is unnecessary upon use.

Although the matching markers 434 are used as the matching means in the present embodiment, a radiopaque material may be applied to the surface of the impression resin accommodation part 430, the jig fastening part 440, or the grip part 460, or they themselves may be made of a radiopaque material.

According to the present invention, since only the CT image is utilized without the oral scan image in manufacturing the guide unlike the conventional method, it is possible to significantly simplify the operation, to significantly reduce the operating time, to constantly maintain accuracy or precision, and to significantly reduce the time required for implant surgery.

While the present invention has been described with respect to the specific embodiments, it will be apparent to those skilled in the art that various changes and modifications may be made by adding, changing, or removing components without departing from the spirit and scope of the invention as defined in the following claims, and these variations and modifications fall within the spirit and scope of the invention as defined in the appended claims.

What is claimed is:

1. A preliminary guide comprising:
an impression resin used to mold an implant placement region in a pattern form, wherein the impression resin comprises 45.27 wt % of urethane dimethacrylate, 20.0 wt % of triethylene glycol dimethacrylate, 15.1 wt % of bisphenol A-glycidyl methacrylate, 18.0 wt % of silica, 1.5 wt % of barium glass, 0.05 wt % of camphorquinone, 0.02 wt % of 2,6-ditert-butyl-4-methylphenol, and 0.06 wt % of ethyl 4-dimethylaminobenzoate; and
a guide tray comprising an impression resin accommodation part configured to accommodate the impression resin therein, and a jig fastening part fastened to a working jig in processing equipment when a placement guide hole is machined to complete a guide.

2. The preliminary guide according to claim 1, the guide tray further comprises a protective cover part configured to prevent a portion of the impression resin from being pushed out and adhering to the jig fastening part due to pressing when the implant placement region is molded in the pattern form in the impression resin.

3. The preliminary guide according to claim 2, wherein the protective cover part is configured such that one side of an extension is slightly raised to prevent the impression resin from being pushed out toward the protective cover part.

4. The preliminary guide according to claim 1, the guide tray further comprises a grip part configured to selectively break upon use.

5. The preliminary guide according to any one of claims 1 to 4, wherein, as the impression resin, a dental resin is used that is cured naturally or artificially after use in a soft state before use.

6. The preliminary guide according to any one of claims 1 to 4, wherein a curing accelerator is added to the impression resin to reduce a curing time.

7. The preliminary guide according to claim 6, wherein the curing accelerator is added in advance before use or additionally added during use.

8. The preliminary guide according to any one of claims 1 to 4, wherein an exposed surface of the impression resin is covered by a thin film.

9. The preliminary guide according to claim 8, wherein the film is made of transparent or translucent vinyl.

10. The preliminary guide according to claim 8, wherein the film has a thickness of 0.03 mm to 0.20 mm.

11. The preliminary guide according to any one of claims 1 to 4, wherein the impression resin accommodation part has a shape corresponding to an upper incisor/premolar region or a lower incisor/premolar region, a shape corresponding to an upper central incisor to second molar region or a lower central incisor to second molar region, a shape corresponding to an upper premolar/molar region or a lower premolar/molar region, or a shape corresponding to an upper central incisor to second molar region or a lower central incisor to second molar region.

* * * * *